(12) United States Patent
Steurer et al.

(10) Patent No.: US 7,902,183 B2
(45) Date of Patent: *Mar. 8, 2011

(54) THIAZOLYL-DIHYDRO-INDAZOLE

(75) Inventors: Steffen Steurer, Vienna (AT); Bodo Betzemeier, Bad Fischau (AT); Darryl McConnell, Vienna (AT); Thomas Gerstberger, Vienna (AT); Matthias Grauert, Biberach (DE); Matthias Hoffmann, Mittelbiberach (DE); Maria Impagnatiello, Vienna (AT); Lars van der Veen, Vienna (AT); Ulrike Weyer-Czernilofsky, Baden (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 753 days.

This patent is subject to a terminal disclaimer.

(21) Appl. No.: 11/696,892

(22) Filed: Apr. 5, 2007

(65) Prior Publication Data

US 2007/0270401 A1 Nov. 22, 2007

(30) Foreign Application Priority Data

Apr. 6, 2006 (EP) .................................. 06112303

(51) Int. Cl.
*A61K 31/43* (2006.01)
*A61K 31/497* (2006.01)
*C07D 513/04* (2006.01)

(52) U.S. Cl. .............. 514/211.08; 514/232.8; 514/253.1; 514/318; 514/338; 514/366; 544/124; 544/133; 546/194; 546/270.1; 548/151

(58) Field of Classification Search ........ None
See application file for complete search history.

(56) References Cited

U.S. PATENT DOCUMENTS

2006/0106013 A1  5/2006  Breitfelder et al.

FOREIGN PATENT DOCUMENTS

| CA | 25979288 A1 | 4/2006 |
|---|---|---|
| DE | 102004048877 A1 | 4/2006 |
| WO | 0157008 A1 | 8/2001 |
| WO | 2006040281 A1 | 4/2006 |

OTHER PUBLICATIONS

International Search Report (Form PCT/ISA/220) for corresponding PCT/EP2007/053092.

*Primary Examiner* — Kamal A Saeed
(74) *Attorney, Agent, or Firm* — Michael P. Morris; Philip I. Datlow

(57) ABSTRACT

The present invention encompasses compounds of general formula (1)

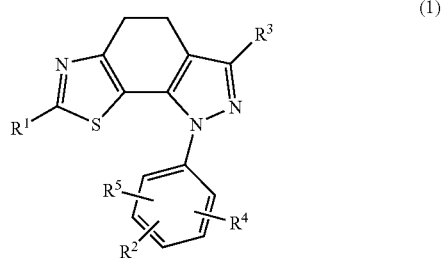

wherein
$R^1$ to $R^5$ are defined as in claim 1, which are suitable for the treatment of diseases characterized by excessive or abnormal cell proliferation, and the use thereof for preparing a medicament having the above-mentioned properties.

11 Claims, No Drawings

THIAZOLYL-DIHYDRO-INDAZOLE

This application claims priority of EP 06112303, filed Apr. 6, 2006.

The present invention relates to new thiazolyl-dihydro-indazoles of general formula (1)

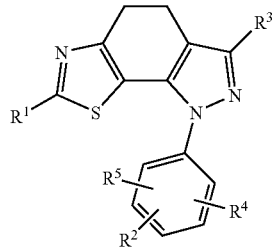

(1)

wherein the groups $R^1$ to $R^5$ have the meanings given in the claims and specification, the isomers thereof, processes for preparing these thiazolyl-dihydro-indazoles and their use as medicaments.

BACKGROUND TO THE INVENTION

The phosphorylation of proteins and lipids is an important cellular regulation mechanism which plays a role in many different biological processes such as cell proliferation, differentiation, apoptosis, metabolism, inflammation, immune reactions and angiogenesis. More than 500 kinases are encoded in the human genome. In general, tyrosine protein kinases are stimulated by growth factors or other mitogenic signals and phosphorylate proteins which initiate rapid signal transmissions. Serine/threonine protein kinases mostly phosphorylate proteins which crosslink and amplify intracellular signals. Lipid kinases are likewise important switching sites in intracellular signal pathways, with these sites linking various biological processes.

A number of protein kinases have already proved to be suitable target molecules for therapeutic intervention in a variety of indications, e.g. cancer and inflammatory and autoimmune diseases. Since a high percentage of the genes involved in the development of cancer which have been identified thus far encode kinases, these enzymes are attractive target molecules for the therapy of cancer in particular.

DETAILED DESCRIPTION OF THE INVENTION

It has now surprisingly been found that compounds of general formula (1), wherein the groups $R^1$ to $R^5$ have the meanings given below, act as inhibitors of specific cell cycle kinases. Thus, the compounds according to the invention may be used for example for the treatment of diseases connected with the activity of specific cell cycle kinases and characterised by excessive or abnormal cell proliferation.

The present invention relates to compounds of general formula (1)

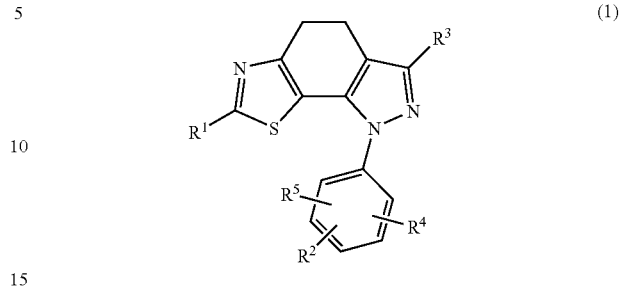

(1)

wherein $R^1$ is selected from among —$NHR^c$, —$NHC(O)R^c$, —$NHC(O)OR^c$, —$NHC(O)NR^cR^c$ and —$NHC(O)SR^c$, and $R^2$ denotes $C_{1-6}$alkyl or 3-8 membered heterocycloalkyl, optionally substituted by one or more $R^6$, or a group selected from among halogen, —$NO_2$, —$NR^cR^c$, —$OR^c$, —$S(O)R^c$, —$S(O)_2R^c$, —$C(O)R^c$, —$C(O)OR^c$, —$C(O)NR^cR^c$, —$C(O)N(R^g)OR^c$ —$N(R^g)C(O)R^c$, —$N(R^g)C(O)OR^c$, —$NR^gC(O)NR^cR^c$, —$N(R^g)C(O)SR^c$ and —$N(R^g)S(O)_2R^c$, and $R^3$ denotes a group selected from among $C_{6-10}$aryl and 5-6 membered heteroaryl, optionally substituted by one or more $R^c$ and/or $R^b$, which may be identical or different, and $R^4$ denotes a group selected from among bromine, fluorine, —$CF_3$, —$OCF_3$, —$CN$, —$NR^cR^c$, —$SR^c$, —$S(O)R^c$, —$S(O)_2R^c$ and —$OR^c$, or $C_{1-3}$alkyl optionally substituted by fluorine, —$CN$, —$NR^fR^f$ and/or —$OR^f$, and $R^5$ denotes hydrogen or a group selected from among halogen, —$CF_3$, —$OCF_3$, —$CN$, —$NR^cR^c$, —$SR^c$, —$S(O)R^c$, —$S(O)_2R^c$ and —$OR^c$, or $C_{1-3}$alkyl optionally substituted by fluorine, —$CN$, —$NR^fR^f$ and/or —$OR^f$, and $R^6$ denotes a group selected from among $R^a$, $R^b$ and $R^a$ substituted by one or more $R^c$ and/or $R^b$, which may be identical or different, and each $R^a$ independently of one another is selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, and each $R^b$ denotes a suitable group independently selected in each case from among =O, —$OR^c$, $C_{1-3}$haloalkyloxy, —$OCF_3$, =S, —$SR^c$, =$NR^c$, =$NOR^c$, —$NR^cR^c$, halogen, —$CF_3$, —$CN$, —$NC$, —$NO_2$, —$N_3$, —$S(O)R^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)_2NR^cR^c$, —$C(O)R^c$, —$C(O)OR^c$, —$C(O)NR^cR^c$, —$C(O)N(R^g)NR^cR^c$, —$C(O)N(R^g)OR^c$, —$CN(R^g)NR^cR^c$, —$OC(O)R^c$, —$OC(O)OR^c$, —$OC(O)NR^cR^c$, —$N(R^g)C(O)R^c$, —$N(R^g)C(O)R^c$, —$N(R^g)C(S)R^c$, —$N(R^g)S(O)_2R^c$, —$N(R^g)S(O)_2NR^cR^c$, —$N(R^g)C(O)OR^c$, —$N(R^g)C(O)NR^cR^c$, and —$N(R^g)CN(R^g)NR^cR^c$, and each $R^c$ independently of one another denote hydrogen or a group optionally substituted by one or more, identical or different $R^d$ and/or $R^e$ selected from among $C_{1-6}$alkyl, $C_{3-8}$cycloalkyl, $C_{4-11}$-cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, each $R^d$ independently of one another denotes a group optionally substituted by one or more, identical or different $R^e$ and/or $R^f$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, and each $R^e$ denotes a suitable group each independently selected from among =O, —$OR^f$, $C_{1-3}$haloalkyloxy, —$OCF_3$, =S, —$SR^f$, =$NR^f$, =$NOR^f$, —$NR^fR^f$, halogen, —$CF_3$, —CN, —NC, —$NO_2$, —$N_3$, —$S(O)R^f$, —$S(O)_2R^f$, —$S(O)_2OR^f$, —$S(O)NR^fR^f$, —$S(O)_2NR^fR^f$, —$OS(O)R^f$, —$OS(O)_2R^f$, —$OS(O)_2OR^f$, —$OS(O)_2NR^fR^f$, —$C(O)R^f$, —$C(O)OR^f$, —$C(O)NR^fR^f$, —$C(O)N(R^g)OR^f$, —$CN(R^g)NR^fR^f$, —$OC(O)R^f$, —$OC(O)OR^f$, —$OC(O)NR^fR^f$, —$OCN(R^g)NR^fR^f$, —$N(R^g)C(O)R^f$, —$N(R^g)C(S)R^f$, —$N(R^g)S(O)_2R^f$, —$N(R^g)C(O)OR^f$, —$N(R^g)C(O)NR^fR^f$, and —$N(R^g)CN(R^g)NR^fR^f$, and each $R^f$ independently of one another denotes hydrogen or a group optionally substituted by one or more, identical or different $R^g$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, and each $R^g$ independently of one another denotes hydrogen, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, optionally in the form of the tautomers, the racemates, the enantiomers, the diastereomers and the mixtures thereof, as well as optionally the pharmacologically acceptable salts thereof, with the proviso that following compounds are not included:

4-(7-acetylamino-3-pyridin-3-yl-4,5-dihydro-pyrazolo[4,3-g]benzothiazol-1-yl)-3-fluoro-N-(2-methoxy-ethyl)-N-methyl-benzamide, N-{1-[2-fluoro-4-(morpholino-4-carbonyl)-phenyl]-3-pyridin-3-yl-4,5-dihydro-1H-pyrazolo[4,3-g]benzothiazol-7-yl}-acetamide, 4-(7-acetylamino-3-pyridin-3-yl-4,5-dihydro-pyrazolo[4,3-g]benzothiazol-1-yl)-3-fluoro-N,N-dimethyl-benzamide, 4-(7-acetylamino-3-pyridin-3-yl-4,5-dihydro-pyrazolo[4,3-g]benzothiazol-1-yl)-N-ethyl-3-fluoro-N-methyl-benzamide, 4-(7-acetylamino-3-pyridin-3-yl-4,5-dihydro-pyrazolo[4,3-g]benzothiazol-1-yl)-N-ethyl-3-fluoro-N-(2-methoxy-ethyl)-benzamide, N-{1-[2-fluoro-4-([1,4]oxazepan-4-carbonyl)-phenyl]-3-pyridin-3-yl-4,5-dihydro-1H-pyrazolo[4,3-g]benzothiazol-7-yl}-acetamide, 4-(7-acetylamino-3-pyrazin-3-yl-4,5-dihydro-pyrazolo[4,3-g]benzothiazol-1-yl)-3,N,N-trimethyl-benzamide, 4-(7-acetylamino-3-pyridin-3-yl-4,5-dihydro-pyrazolo[4,3-g]benzothiazol-1-yl)-2-methoxy-N-(4-pyrrolidin-1-yl-cyclohexyl)-benzamide, 4-(7-acetylamino-3-pyridin-3-yl-4,5-dihydro-pyrazolo[4,3-g]benzothiazol-1-yl)-2-methoxy-N-methyl-N-(4-pyrrolidin-1-yl-cyclohexyl)-benzamide, 4-(7-acetylamino-3-pyridin-3-yl-4,5-dihydro-pyrazolo[4,3-g]benzothiazol-1-yl)-N-(1-cyclopentyl-piperidin-4-yl)-2-methoxy-benzamide, 4-(7-acetylamino-3-pyridin-3-yl-4,5-dihydro-pyrazolo[4,3-g]benzothiazol-1-yl)-N-(1-cyclopentyl-piperidin-4-yl)-2-methoxy-N-methyl-benzamide, N-(1-{4-[4-(cyclopentyl-methyl-amino)-piperidine-1-carbonyl]-3-methoxy-phenyl}-3-pyridin-3-yl-4,5-dihydro-1H-pyrazolo[4,3-g]benzothiazol-7-yl)-acetamide, 4-(7-acetylamino-3-pyridin-3-yl-4,5-dihydro-pyrazolo[4,3-g]benzothiazol-1-yl)-N,N-diethyl-3-fluoro-benzamide, 4-(7-acetylamino-3-pyridin-3-yl-4,5-dihydro-pyrazolo[4,3-g]benzothiazol-1-yl)-3-fluoro-N-(2-methoxy-ethyl)-benzamide, 4-(7-acetylamino-3-pyridin-3-yl-4,5-dihydro-pyrazolo[4,3-g]benzothiazol-1-yl)-3-fluoro-N-(2-pyrrolidin-1-yl-ethyl)-benzamide, N-{1-[4-(4-dimethylamino-piperidine-1-carbonyl)-2-fluoro-phenyl]-3-pyridin-3-yl-4,5-dihydro-1H-pyrazolo[4,3-g]benzothiazol-7-yl}-acetamide, 4-(7-acetylamino-3-pyridin-3-yl-4,5-dihydro-pyrazolo[4,3-g]benzothiazol-1-yl)-3-fluoro-N-methyl-N-(1-methyl-piperidin-4-yl)-benzamide, 4-(7-acetylamino-3-pyridin-3-yl-4,5-dihydro-pyrazolo[4,3-g]benzothiazol-1-yl)-N-(2-dimethylamino-ethyl)-3-fluoro-benzamide, 4-(7-acetylamino-3-pyridin-3-yl-4,5-dihydro-pyrazolo[4,3-g]benzothiazol-1-yl)-N-(3-dimethylamino-propyl)-3-fluoro-N-methyl-benzamide, 4-(7-acetylamino-3-pyridin-3-yl-4,5-dihydro-pyrazolo[4,3-g]benzothiazol-1-yl)-N-(2-dimethylamino-ethyl)-3-fluoro-N-methyl-benzamide, N-{1-[2-fluoro-4-(4-isopropyl-piperazine-1-carbonyl)-phenyl]-3-pyridin-3-yl-4,5-dihydro-1H-pyrazolo[4,3-g]benzothiazol-7-yl}-acetamide, 4-(7-acetylamino-3-pyridin-3-yl-4,5-dihydro-pyrazolo[4,3-g]benzothiazol-1-yl)-N,N-diethyl-3-fluoro-benzamide, N-{1-[4-(4-cyclopentyl-piperazine-1-carbonyl)-2-fluoro-phenyl]-3-pyridin-3-yl-4,5-dihydro-1H-pyrazolo[4,3-g]benzothiazol-7-yl}-acetamide, N-(1-{4-[4-(1-ethyl-propyl)-piperazine-1-carbonyl]-2-fluoro-phenyl}-3-pyridin-3-yl-4,5-dihydro-1H-pyrazolo[4,3-g]benzothiazol-7-yl)-acetamide, N-{1-[4-(4-sec-butyl-piperazine-1-carbonyl)-2-fluoro-phenyl]-3-pyridin-3-yl-4,5-dihydro-1H-pyrazolo[4,3-g]benzothiazol-7-yl}-acetamide, 2-{4-[4-(7-acetylamino-3-pyridin-3-yl-4,5-dihydro-pyrazolo[4,3-g]benzothiazol-1-yl)-3-fluoro-benzoyl]-piperazin-1-yl}-N,N-dimethyl-acetamide, 4-(7-acetylamino-3-pyridin-3-yl-4,5-dihydro-pyrazolo[4,3-g]benzothiazol-1-yl)-3-fluoro-N-(3-morpholin-4-yl-cyclobutyl)-benzamide, N-{1-[2-fluoro-4-(4-methyl-piperazine-1-carbonyl)-phenyl]-3-pyridin-3-yl-4,5-dihydro-1H-pyrazolo[4,3-g]benzothiazol-7-yl}-acetamide, 4-(7-acetylamino-3-pyridin-3-yl-4,5-dihydro-pyrazolo[4,3-g]benzothiazol-1-yl)-3-fluoro-N,N-dimethyl-benzamide, N-[4-(7-acetylamino-3-pyridin-3-yl-4,5-dihydro-pyrazolo[4,3-g]benzothiazol-1-yl)-3-fluoro-phenyl]-2-dimethylamino-acetamide, N-[1-(4-acetylamino-2-fluoro-phenyl)-3-pyridin-3-yl-4,5-dihydro-1H-pyrazolo[4,3-g]benzothiazol-7-yl]-acetamide, 3-fluoro-4-[7-(3-methoxy-propionylamino)-3-pyridin-3-yl-4,5-dihydro-pyrazolo[4,3-g]benzothiazol-1-yl]-N,N-dimethyl-benzamide and 3-fluoro-N,N-dimethyl-4-[7-(3-phenyl-propionylamino)-3-pyridin-3-yl-4,5-dihydro-pyrazolo[4,3-g]benzothiazol-1-yl]-benzamide.

One aspect of the invention relates to compounds of general formula (1A),

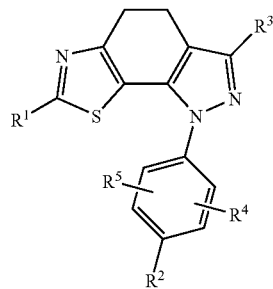

(1A)

wherein the substituents are as hereinbefore defined.

One aspect of the invention relates to compounds of general formula (1B),

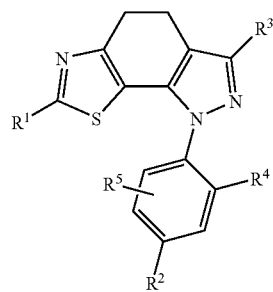

(1B)

wherein the substituents are as hereinbefore defined.

One aspect of the invention relates to compounds of general formula (1), (1A) or (1B), wherein $R^3$ denotes 5-6 membered heteroaryl, optionally substituted by one or more $R^c$ and/or $R^b$, which may be identical or different.

One aspect of the invention relates to compounds of general formula (1), (1A) or (1B), wherein $R^3$ denotes unsubstituted pyridyl.

One aspect of the invention relates to compounds of general formula (1), (1A) or (1B), wherein $R^1$ is selected from among —NHC(O)$R^c$, —NHC(O)O$R^c$ and —NHC(O)N$R^c$$R^c$.

(A) Aspects Relating to $R^1$ (A1) One aspect of the invention relates to compounds of general formula (1), (1A) or (1B), wherein $R^1$ denotes —NHC(O)CH$_3$.

(A2) Another aspect of the invention relates to compounds of general formula (1), (1A) or (1B), wherein $R^1$ denotes —NHC(O)OCH$_3$.

(B) Aspects Relating to $R^2$ (B1) One aspect of the invention relates to compounds of general formula (1), (1A) or (1B), wherein $R^2$ denotes —C(O)N$R^c$$R^c$.

(B2) Another aspect of the invention relates to compounds of general formula (1), (1A) or (1B), wherein $R^2$ denotes —C(O)NH$R^c$ and $R^c$ denotes methyl, $C_{1-3}$alkyl, optionally substituted by —O$R^f$, —N$R^f$$R^f$, 3-8 membered heterocycloalkyl, optionally substituted by methyl.

(B3) Another aspect of the invention relates to compounds of general formula (1), (1A) or (1B), wherein $R^2$ denotes —C(O)N(CH$_3$)$R^c$ and $R^c$ denotes methyl, $C_{1-3}$alkyl, optionally substituted by O$R^f$ or N$R^f$$R^f$ or heterocycloalkyl, optionally substituted by methyl.

(B4) Another aspect of the invention relates to compounds of general formula (1), (1A) or (1B), wherein $R^2$ denotes —C(O)$R^c$ and $R^c$ denotes 3-8 membered heterocycloalkyl, optionally substituted by $C_{1-3}$alkyl or —N$R^f$$R^f$, 5-6 membered heteroaryl or (5-6 membered heteroaryl)-methyl.

(B5) Another aspect of the invention relates to compounds of general formula (1), (1A) or (1B), wherein $R^2$ denotes —NHC(O)$R^c$ and $R^c$ denotes $C_{1-4}$alkyl, optionally substituted by —O$R^f$ or —N$R^f$$R^f$, 3-8 membered cycloalkyl, 3-8 membered heterocycloalkyl, optionally substituted by methyl or 5-6 membered heteroaryl, optionally substituted by methyl.

(B6) Another aspect of the invention relates to compounds of general formula (1), (1A) or (1B), wherein $R^2$ denotes —NHC(O)O$R^c$ and $R^c$ denotes $C_{1-4}$alkyl, optionally substituted by —O$R^f$ or —N$R^f$$R^f$, 3-8 membered cycloalkyl, 3-8 membered heterocycloalkyl, optionally substituted by methyl or 5-6 membered heteroaryl, optionally substituted by methyl.

(C) Aspects Relating to $R^4$ (C1) One aspect of the invention relates to compounds of general formula (1), (1A) or (1B), wherein $R^4$ denotes fluorine.

(C2) Another aspect of the invention relates to compounds of general formula (1), (1A) or (1B), wherein $R^4$ denotes bromine.

(D) Aspects Relating to $R^5$ (D1) One aspect of the invention relates to compounds of general formula (1), (1A) or (1B), wherein $R^5$ denotes hydrogen.

(D2) One aspect of the invention relates to compounds of general formula (1), (1A) or (1B), wherein $R^5$ denotes fluorine.

One aspect of the invention relates to compounds of general formula (1), (1A) or (1B), or the pharmaceutically effective salts thereof, as medicaments.

One aspect of the invention relates to compounds of general formula (1), (1A) or (1B), or the pharmacologically effective salts thereof, for preparing a medicament with an antiproliferative activity.

One aspect of the invention is a pharmaceutical preparation, containing as active substance one or more compounds of general formula (1), (1A) or (1B), or the pharmacologically effective salts thereof, optionally in combination with conventional excipients and/or carriers.

One aspect of the invention is the use of compounds of general formula (1), (1A) or (1B) for preparing a medicament for the treatment and/or prevention of cancer.

One aspect of the invention is a pharmaceutical preparation comprising a compound of general formula (1), (1A) or (1B) and at least one other cytostatic or cytotoxic active substance different from formula (1), (1A) or (1B), optionally in the form of the tautomers, the racemates, the enantiomers, the diastereomers and the mixtures thereof, as well as optionally the pharmacologically acceptable salts thereof.

DEFINITIONS

As used herein the following definitions apply, unless stated otherwise.

By alkyl substituents are meant in each case saturated, unsaturated, straight-chain or branched aliphatic hydrocarbon groups (alkyl group) and this includes both saturated alkyl groups and unsaturated alkenyl and alkynyl groups. Alkenyl substituents are in each case straight-chain or branched, unsaturated alkyl groups, which have at least one double bond. By alkynyl substituents are meant in each case straight-chain or branched, unsaturated alkyl groups, which have at least one triple bond.

The term heteroalkyl refers to groups which can be derived from alkyl as defined above in its broadest sense by replacing one or more of the groups —CH$_3$ in the hydrocarbon chains independently of one another by the groups —OH, —SH or —NH$_2$, one or more of the groups —CH$_2$— independently of one another by the groups —O—, —S— or —NH—, one or more of the groups

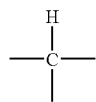

by the group

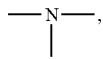

one or more of the groups =CH— by the group =N—, one or more of the groups =CH$_2$ by the group =NH or one or more of the groups =CH by the group =N, while in all only a maximum of three heteroatoms may be present in a heteroalkyl, there must be at least one carbon atom between two oxygen and between two sulphur atoms or between one oxygen and one sulphur atom and the group as a whole must have chemical stability.

It flows from the indirect definition/derivation from alkyl that heteroalkyl is made up of the sub-groups of saturated hydrocarbon chains with hetero-atom(s), heteroalkenyl and heteroalkynyl, while further subdivision into straight-chain (unbranched) and branched may be carried out. If a heteroalkyl is supposed to be substituted, the substitution may take place independently of one another, in each case mono- or polysubstituted, at all the hydrogen-carrying oxygen, sulphur, nitrogen and/or carbon atoms. Heteroalkyl itself may be linked to the molecule as substituent both through a carbon atom and through a heteroatom.

By way of example, the following representative compounds are listed: dimethylaminomethyl; dimethylaminoethyl (1-dimethylaminoethyl; 2-dimethylaminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl (1-diethylaminopropyl, 2-diethylamino-propyl, 3-diethylaminopropyl); diisopropylaminoethyl (1-diisopropylaminoethyl, 2-di-isopropylaminoethyl); bis-2-methoxyethylamino; [2-(dimethylamino-ethyl)-ethyl-amino]-methyl; 3-[2-(dimethylamino-ethyl)-ethyl-amino]-propyl; hydroxymethyl; 2-hydroxyethyl; 3-hydroxypropyl; methoxy; ethoxy; propoxy; methoxymethyl; 2-methoxyethyl etc.

Haloalkyl relates to alkyl groups, wherein one or more hydrogen atoms are replaced by halogen atoms. Haloalkyl includes both saturated alkyl groups and unsaturated alkenyl and alkynyl groups, such as for example —CF$_3$, —CHF$_2$, —CH$_2$F, —CF$_2$CF$_3$, —CHFCF$_3$, —CH$_2$CF$_3$, —CF$_2$CH$_3$, —CHFCH$_3$, —CF$_2$CF$_2$CF$_3$, —CF$_2$CH$_2$CH$_3$, —CF=CF$_2$, —CCl=CH$_2$, —CBr=CH$_2$, —CI=CH$_2$, —C≡C—CF$_3$, —CHFCH$_2$CH$_3$ and —CHFCH$_2$CF$_3$.

Halogen refers to fluorine, chlorine, bromine and/or iodine atoms.

By cycloalkyl is meant a mono or bicyclic ring, while the ring system may be a saturated ring or, however, an unsaturated, non-aromatic ring, which may optionally also contain double bonds, such as for example cyclopropyl, cyclopropenyl, cyclobutyl, cyclobutenyl, cyclopentyl, cyclopentenyl, cyclohexyl, cyclohexenyl, norbornyl and norbornenyl.

Cycloalkylalkyl includes a non-cyclic alkyl group wherein a hydrogen atom bound to a carbon atom, usually to a terminal C atom, is replaced by a cycloalkyl group.

Aryl relates to monocyclic or bicyclic aromatic ring systems with 6-10 carbon atoms such as phenyl and naphthyl, for example.

Arylalkyl includes a non-cyclic alkyl group wherein a hydrogen atom bound to a carbon atom, usually to a terminal C atom, is replaced by an aryl group.

By heteroaryl are meant mono- or bicyclic aromatic ring systems, which instead of one or more carbon atoms contain one or more, identical or different hetero atoms, such as e.g. nitrogen, sulphur or oxygen atoms. Examples include furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl and benzotriazinyl, indolizinyl, oxazolopyridyl, imidazopyridyl, naphthyridinyl, indolinyl, isochromanyl, chromanyl, tetrahydroisoquinolinyl, isoindolinyl, isobenzotetrahydrofuryl, isobenzotetrahydrothienyl, isobenzothienyl, benzoxazolyl, pyridopyridyl, benzotetrahydrofuryl, benzotetrahydrothienyl, purinyl, benzodioxolyl, triazinyl, phenoxazinyl, phenothiazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridyl-N-oxide tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide.

Heteroarylalkyl encompasses a non-cyclic alkyl group wherein a hydrogen atom bound to a carbon atom, usually to a terminal C atom, is replaced by a heteroaryl group.

Heterocycloalkyl relates to saturated or unsaturated, non-aromatic mono-, bicyclic or bridged bicyclic rings comprising 3-12 carbon atoms, which instead of one or more carbon atoms carry heteroatoms, such as nitrogen, oxygen or sulphur. Examples of such heterocycloalkyl groups are tetrahydrofuryl, pyrrolidinyl, pyrrolinyl, imidazolidinyl, imidazolinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, tetrahydropyranyl, tetrahydrothienyl, homothiomorpholinyl-S,S-dioxide, oxazolidinonyl, dihydropyrazolyl, dihydropyrrolyl, dihydropyrazinyl, dihydropyridyl, dihydropyrimidinyl, dihydrofuryl, dihydropyranyl, tetrahydrothienyl-S-oxide, tetrahydrothienyl-S,S-dioxide, homothiomorpholinyl-S-oxide, 2-oxa-5-azabicyclo[2,2,1]heptane, 8-oxa-3-aza-bicyclo[3.2.1]octane, 3.8-diaza-bicyclo[3.2.1]octane, 2,5-diaza-bicyclo[2,2,1]heptane, 3.8-diaza-bicyclo[3.2.1]octane, 3.9-diaza-bicyclo[4.2.1]nonane and 2.6-diaza-bicyclo[3.2.2]nonane.

Heterocycloalkylalkyl relates to a non-cyclic alkyl group wherein a hydrogen atom bound to a carbon atom, usually to a terminal C atom, is replaced by a heterocycloalkyl group.

The following Examples illustrate the present invention without restricting its scope.

Synthesis of the Reagents

The following compounds have already been described in the applications PCT/EP05055021 or PCT/EP05055015.

| # | structure |
|---|---|
| H-1) | 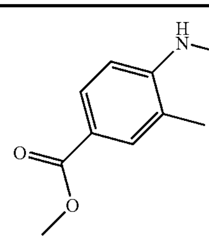 |
| Z-1) | 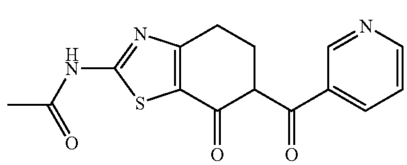 |
| Z-2) | 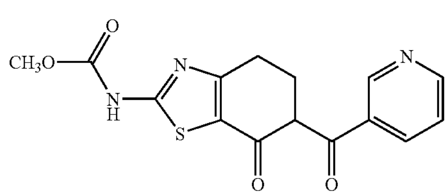 |
| Z-3) | 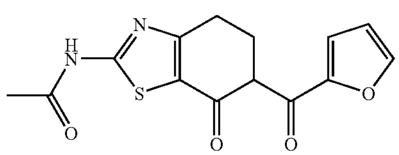 |

H-2) methyl 3-bromo-4-hydrazino-benzoate

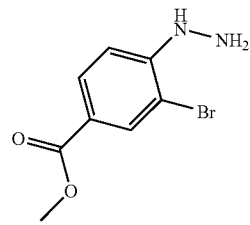

Methyl-4-amino-3-bromobenzoate (32 g, 139 mmol) is combined with 250 mL conc. hydrochloric acid and cooled to −10° C. A solution of sodium nitrite (10.2 g, 146 mmol) in 120 mL water is added dropwise such that the temperature does not exceed −5° C. After 40 min stirring at −10° C. a solution of tin(II)chloride dihydrate (128 g, 556 mmol) in 130 mL conc. hydrochloric acid is added dropwise to the suspension, while the reaction temperature does not exceed −5° C. The thick liquid suspension is stirred for 1.5 h at RT, before being adjusted to pH 10 with NaOH (12 N). The reaction mixture is combined with 500 mL dichloromethane and water and after 30 min stirring it is filtered. The filter cake is combined with 300 mL dichloromethane and 100 mL water and refluxed for 30 min. After filtration the filtrate is extracted with chloroform. The combined organic phases are dried on magnesium sulphate, filtered and evaporated to dryness. Yield: 34 g.

H-3) 2,5-difluoro-4-hydrazino-benzoic acid

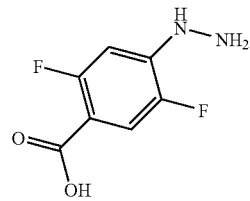

Starting from 4-nitro-2,5-difluorobenzoic acid (2.5 g, 12.3 mmol) the corresponding aniline compound 4-amino-2,5-difluorobenzoic acid is obtained by catalytic hydrogenation with 10% palladium on activated charcoal (300 mg) in 100 mL methanol at 4 bar hydrogen pressure after filtration and evaporation of the solvent. Yield: 2.1 g.

Analogously to the preparation of H-2 the desired product H-3 is obtained starting from 4-amino-2,5-difluorobenzoic acid (1.1 g, 6.6 mmol), sodium nitrite (0.56 g, 7.8 mmol), tin(II)chloride dihydrate (4.4 g, 20 mmol) in a total of 8 mL conc. hydrochloric acid and 12 mL ice water. Yield: 758 mg.

H-4) methyl 2,5-difluoro-4-hydrazino-benzoate

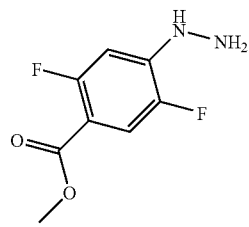

Thionyl chloride (1.5 mL) is slowly added dropwise at 0° C. to 8 mL methanol. This mixture is combined with a solution of 4-amino-2,5-difluorobenzoic acid (0.95 g, 5.5 mmol) in 20 mL methanol over a period of 10 min, then stirred for 30 min at RT and for 3 h at 50° C. After evaporation of the solvent the residue is taken up in ethyl acetate, and this solution is washed 3× with saturated sodium hydrogen carbonate solution, dried on magnesium sulphate and evaporated down. Yield: 1 g methyl-4-amino-2,5-difluorobenzoate Analogously to the preparation of H-2 the desired product H-4 is obtained starting from methyl-4-amino-2,5-difluorobenzoate (1 g, 5.4 mmol), sodium nitrite (0.5 g, 7.5 mmol), tin(II)chloride dihydrate (3.6 g, 16 mmol) in a total of 8 mL conc. hydrochloric acid and 10 mL ice water. Yield: 246 mg.

H-5) 2-bromo-4-isopropylphenylhydrazine

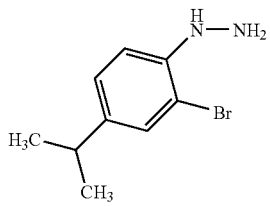

Analogously to the preparation of H-2 the desired product H-5 is obtained starting from 2-bromo-4-isopropylaniline (1 g, 4.5 mmol), sodium nitrite (0.38 g, 5.4 mmol), tin(II)chloride dihydrate (2.6 g, 11.3 mmol) in a total of 55 mL hydrochloric acid (w=0.37) and 20 mL water. Yield: 0.8 g.

H-6) 2-fluoro-4-(2-morpholin-4-yl-ethoxy)-phenyl-hydrazine

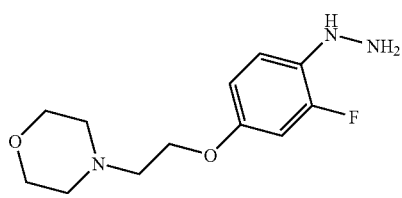

Potassium carbonate (2.7 g, 20 mmol) and N-(2-chloroethyl)morpholine hydrochloride (1.9 g, 10 mmol) are added successively to a solution of 3-fluoro-4-nitrophenol (1.6 g, 10 mmol) in 10 mL DMF. The reaction mixture is stirred for 4 h at 80° C., combined with water and extracted with ethyl acetate. The combined organic phases are washed successively with 1 N NaOH and saturated sodium chloride solution, dried on magnesium sulphate and evaporated down in vacuo. The crude product is purified by chromatography on silica gel with 0-60% ethyl acetate in cyclohexane.

The product thus obtained 4-[2-(3-fluoro-4-nitro-phenoxy)-ethyl]-morpholine (2 g, 7 mmol) is subjected to catalytic hydrogenation with 10% palladium on activated charcoal (0.1 g) in 100 mL methanol under a hydrogen atmosphere, while the 2-fluoro-4-(2-morpholin-4-yl-ethoxy) aniline formed after filtration and evaporation of the solvent is obtained as a solid. Yield: 1.7 g.

A solution of sodium nitrite (0.38 g, 5.4 mmol) in 20 mL water is slowly added dropwise at −15° C. to a solution of 2-fluoro-4-(2-morpholin-4-yl-ethoxy)aniline (1.7 g, 4.5 mmol) in 20 mL conc. hydrochloric acid. The resulting suspension is stirred for 4 h at −10° C., before a solution of tin(II)chloride dihydrate (2.6 g, 11.3 mmol) in 20 mL conc. hydrochloric acid is added dropwise. After 14 h stirring at RT the reaction mixture is adjusted to pH 10 with 10 N NaOH and combined with dichloromethane. After filtration through Celite® the filtrate is extracted with dichloromethane. The combined organic phases are dried on magnesium sulphate and evaporated down in vacuo. Yield: 1.5 g.

H-7) 5-cyano-2,4-difluorophenylhydrazine

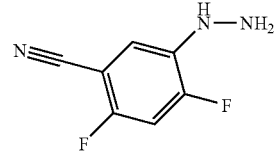

2,4-difluoro-5-nitrobenzonitrile (3 g, 16 mmol) is first of all subjected to catalytic hydrogenation with 5% palladium on activated charcoal (0.25 g) in 250 mL methanol (14 h at 4 bar hydrogen pressure), while the 5-amino-2,4-difluorobenzonitrile formed is obtained as a solid after filtration and evaporation of the solvent. Yield: 2.3 g.

Analogously to the preparation of H-2 the desired product H-7 is obtained, starting from 5-amino-2,4-difluorobenzonitrile (1.4 g, 9 mmol), sodium nitrite (0.8 g, 12 mmol), tin(II) chloride dihydrate (7.2 g, 32 mmol) in a total of 40 mL hydrochloric acid (w=0.32) and 13 mL water. Yield: 0.55 g.

H-8) methyl-3-methoxy-4-hydrazinobenzoate

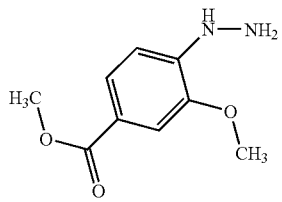

Analogously to the preparation of H-2 the desired product H-8 is obtained starting from methyl-4-amino-3-methoxybenzoate (5.2 g, 28.4 mmol), sodium nitrite (2.2 g, 31 mmol), tin(II)chloride dihydrate (27.6 g, 122 mmol) in a total of 50 mL conc. hydrochloric acid and 25 mL water. Yield: 4.5 g.

All the other reagents used for synthesising the Examples are commercially obtainable or their preparation is known from the literature.

Synthesis of the Examples

I-1) methyl 4-(7-acetylamino-3-pyridin-3-yl-4,5-dihydro-pyrazolo[4,3-g]benzothiazol-1-yl)-3-bromo-benzoate

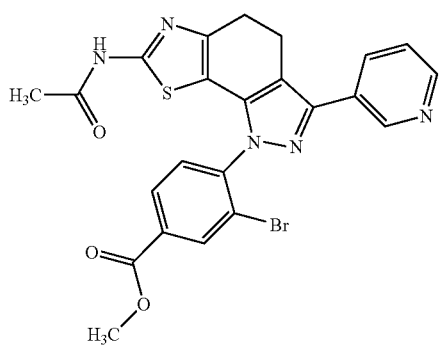

A suspension of Z-1 (10 g, w=0.9, 29 mmol) and H-2 (8 g, 33 mmol) in 30 mL glacial acetic acid is stirred for 15 h at RT. Then the reaction mixture is evaporated down, combined with 60 mL ethanol and stirred for 30 min at 35° C. The suspension is slowly cooled, filtered, the solid obtained is washed with ethanol (3×15 mL) and dried in vacuo. Yield: 11.8 g.

I-2) methyl 3-bromo-4-(7-methoxycarbonylamino-3-pyridin-3-yl-4,5-dihydro-pyrazolo[4,3-g]benzothiazol-1-yl)-benzoate

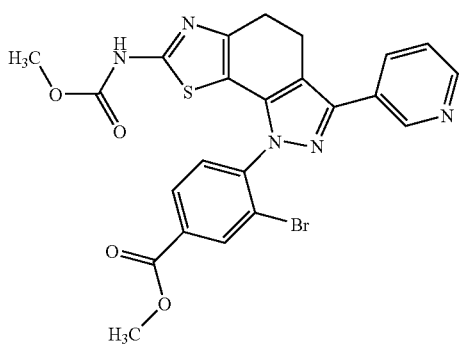

Analogously to the preparation of I-1 the desired compound I-2 is obtained as a solid starting from Z-2 (1.6 g, 4.7 mmol), H-2 (1.16 g, 4.8 mmol) and 15 mL glacial acetic acid. Yield: 2.2 g.

I-3) methyl 3-fluoro-4-(7-methoxycarbonylamino-3-pyridin-3-yl-4,5-dihydro-pyrazolo[4,3-g]benzothiazol-1-yl)-benzoate

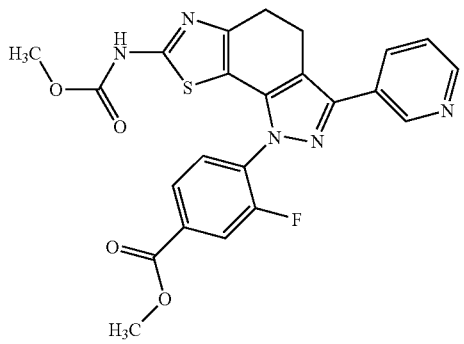

Analogously to the preparation of I-1 the desired compound I-3 is obtained as a solid starting from Z-2 (1 g, 3.0 mmol), H-1 (1.1 g, 6 mmol) and 13 mL glacial acetic acid. Yield: 0.75 g.

I-4) N-[1-(2-fluoro-4-nitro-phenyl)-3-pyridin-3-yl-4,5-dihydro-1H-pyrazolo[4,3-g]benzothiazol-7-yl]-acetamide

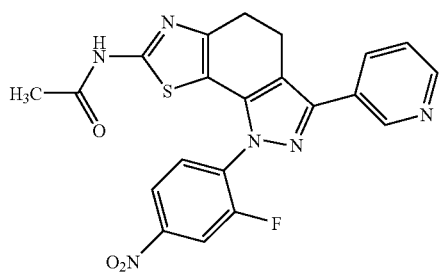

The synthesis is described in PCT/EP05055021.

I-5) 2,5-difluoro-4-(7-methoxycarbonylamino-3-pyridin-3-yl-4,5-dihydro-pyrazolo[4,3-g]benzothiazol-1-yl)-benzoic acid

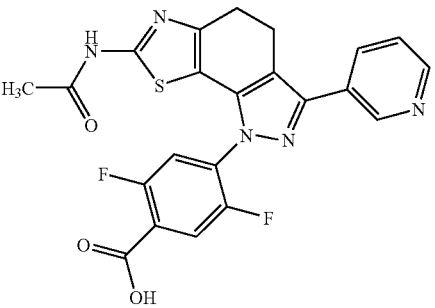

Analogously to the preparation of I-1 the desired compound I-5 is obtained as a solid starting from Z-1 (1 g, 3.3 mmol), H-3 (0.75 mg, 4 mmol) and 20 mL glacial acetic acid. Yield: 0.9 g.

I-6) N-[1-(4-nitro-2-trifluoromethyl-phenyl)-3-pyridin-3-yl-4,5-dihydro-1H-pyrazolo[4,3-g]benzothiazol-7-yl]-acetamide

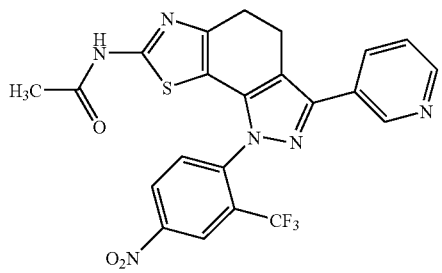

A suspension of Z-1 (1.9 g, 6 mmol) and 4-nitro-2-trifluoromethyl-phenylhydrazine (1.5 g, 6.6 mmol) in 37 mL glacial acetic acid is stirred for 1 h at 60° C. Then the reaction mixture is added to ice water and extracted with ethyl acetate. The combined organic phases are washed with saturated sodium chloride solution, dried on sodium sulphate, filtered and evaporated down in vacuo. The crude product is dissolved in a mixture of 8 mL acetonitrile, 8 mL DMF and 5 mL DMSO and purified by RP-chromatography (gradient:10% acetonitrile/water→98%; 80 min) acetonitrile water in 80 min. The isolated product is then recrystallised from dichloromethane/methanol (5:1). Yield: 340 mg.

I-7) N-[1-(4-nitro-2-trifluoromethyl-phenyl)-3-furan-2-yl-4,5-dihydro-1H-pyrazolo[4,3-g]benzothiazol-7-yl]-acetamide

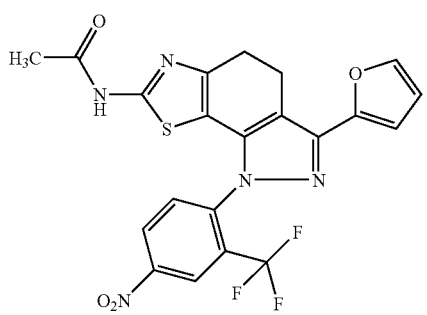

Analogously to the preparation of I-6 the desired product is obtained starting from Z-3 (5 g, 16.4 mmol), 4-nitro-2-trifluoromethyl-phenylhydrazine (4 g, 18 mmol) in 100 mL glacial acetic acid after chromatography on silica gel (cyclohexane/ethyl acetate 60:40→70:30). Yield: 1.3 g.

I-8) methyl 3-methoxy-4-(7-methoxycarbonylamino-3-pyridin-3-yl-4,5-dihydro-pyrazolo[4,3-g]benzothiazol-1-yl)-benzoate

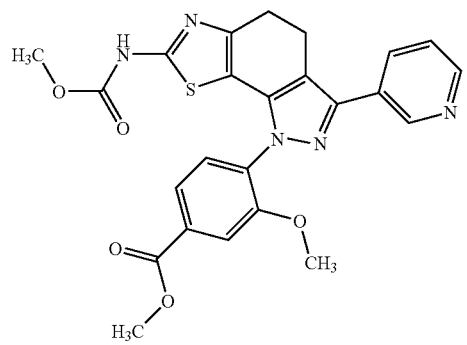

Analogously to the preparation of I-1 the desired compound I-8 is obtained as a solid starting from Z-2 (2.57 g, 7.8 mmol), H-8 (3 g, 15.5 mmol) and 42 mL glacial acetic acid. Yield: 0.96 g.

II-1) 4-(7-acetylamino-3-pyridin-3-yl-4,5-dihydro-pyrazolo[4,3-g]benzothiazol-1-yl)-3-bromo-benzoic acid

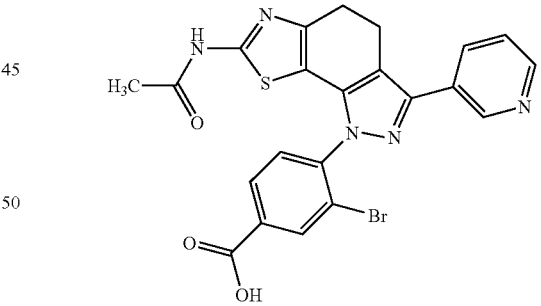

A solution of lithium hydroxide (0.7 g, 29 mmol in 4.3 mL water) is added dropwise to a suspension of I-1 (2.2 g, 4.1 mmol) in dioxane with stirring. After the solution has cleared the reaction mixture is stirred for another 30 min at RT, diluted with 20 mL water and adjusted to pH 5 with 1 N hydrochloric acid. The precipitate formed is filtered, washed with water and dried. The desired product is used without any further purification. Yield: 1.9 g.

The following carboxylic acids are obtained analogously to the preparation of II-1.

| # | educt | structure |
|---|---|---|
| II-2 | I-2 | 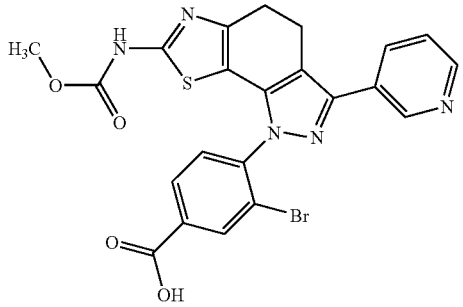 |
| II-3 | I-3 | 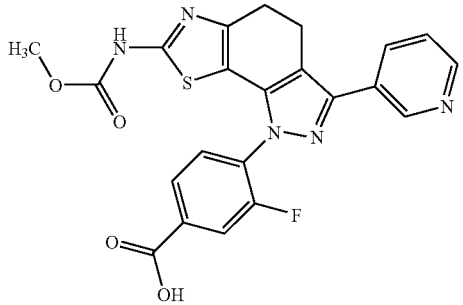 |
| II-4 | I-8 | 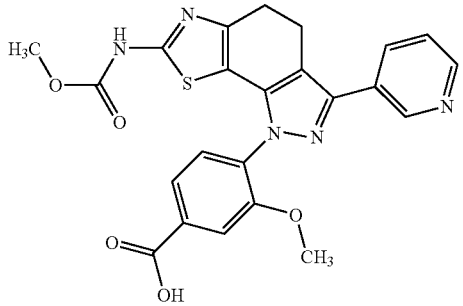 |

III-1) N-[1-(4-amino-2-fluorophenyl)-3-pyridin-3-yl-4,5-dihydro-1H-pyrazolo[4,3-g]benzothiazol-7-yl]-acetamide

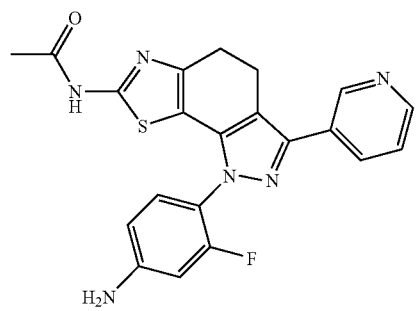

The synthesis is described in PCT/EP05055021.

III-2) 1-(2-fluoro-4-nitro-phenyl)-3-pyridin-3-yl-4,5-dihydro-1H-pyrazolo[4,3-g]benzothiazol-7-ylamine

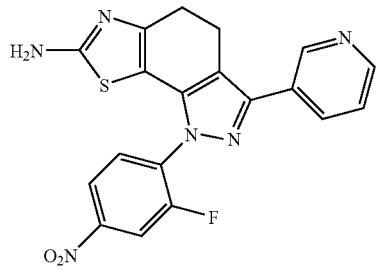

A solution of I-4 (0.5 g, 1.1 mmol) in 6 N hydrochloric acid (10 mL) is stirred for 5 h at 70° C. and then for 14 h at 60° C. After cooling the reaction mixture is made slightly basic with 1 N NaOH and extracted with ethyl acetate. The combined organic phases are dried on magnesium sulphate, filtered and evaporated down in vacuo. The crude product is used without any further purification.

III-3) methyl 1-(2-fluoro-4-nitro-phenyl)-3-pyridin-3-yl-4,5-dihydro-1H-pyrazolo[4,3-g]benzothiazol-7-yl-carbamidate

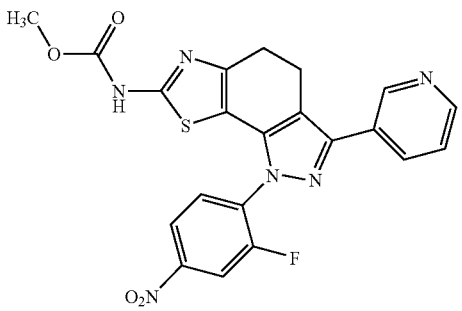

A solution of III-2 (460 mg, 1.1 mmol) in 10 mL pyridine is cooled to −20° C. and combined batchwise with methyl-chloroformate (0.1 mL, 1.3 mmol). After 14 h stirring at RT the precipitate formed is filtered, taken up in acetonitrile and treated for 30 min with ultrasound. The undissolved solid is filtered and dried. Yield: 270 mg.

III-4) methyl 1-(4-amino-2-fluorophenyl)-3-pyridin-3-yl-4,5-dihydro-1H-pyrazolo[4,3-g]benzothiazol-7-yl-carbamidate

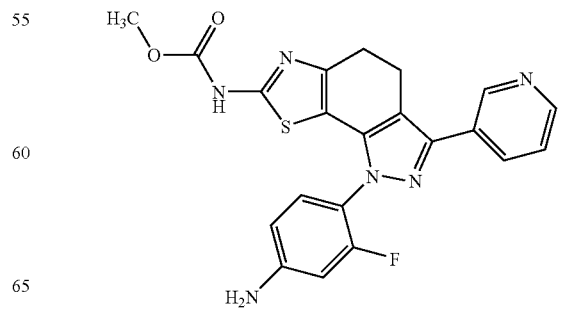

A solution of III-3 (265 mg, 0.6 mmol) in 20 mL THF and 20 mL DMF is combined with 10% platinum on activated charcoal (36 mg) as well as vanadyl acetonate (37 mg, 0.14 mmol) and the mixture is stirred for 14 h at RT under 4 bar hydrogen atmosphere and then filtered. The filtrate is evaporated down in vacuo. Yield: 242 mg III-5) N-1-(4-amino-2-trifluoromethylphenyl)-3-pyridin-3-yl-4,5-dihydro-1H-pyrazolo[4,3-g]benzothiazol-7-yl-acetamide

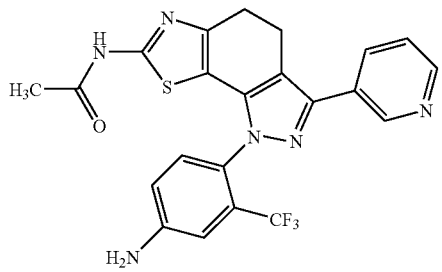

Analogously to the preparation of III-4 the desired product III-5 is obtained starting from I-6 (333 mg, 0.67 mmol), 5% platinum on activated charcoal (75 mg) and vanadyl acetyl acetonate (65 mg, 0.24 mmol) in 50 mL methanol and 10 mL DMF. Yield: 313 mg.

III-6) N-1-(4-amino-2-trifluoromethylphenyl)-3-furan-2-yl-4,5-dihydro-1H-pyrazolo[4,3-g]benzothiazol-7-yl-acetamide

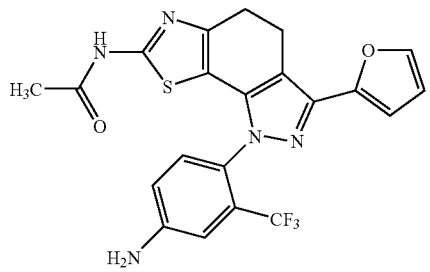

Analogously to the preparation of III-4 the desired product III-6 is obtained starting from I-7 (333 mg, 0.67 mmol), 5% platinum on activated charcoal (75 mg) and vanadyl acetyl acetonate (65 mg, 0.24 mmol) in 50 mL methanol and 10 mL DMF. Yield: 313 mg.

IV-1) N-[4-(7-acetylamino-3-pyridin-3-yl-4,5-dihydro-pyrazolo[4,3-g]benzothiazol-1-yl)-3-fluorophenyl]-2-chloroacetamide

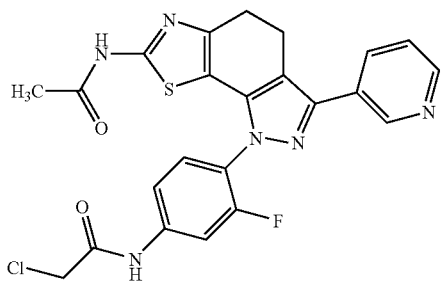

A suspension of III-1 (928 mg, 1.8 mmol) in 20 mL NMP is combined with 0.5 mL diisopropylethylamine and stirred for 5 min at RT. After the addition of 0.54 mL chloroacetyl chloride the mixture is stirred for 1 h at RT, then combined with water and extracted with dichloromethane. The combined organic phases are dried on magnesium sulphate, filtered and evaporated down. After purification by RP-chromatography (gradient: 5% acetonitrile/water→98% acetonitrile/water; 35 min) the fractions containing the product are lyophilised. Yield: 364 mg.

IV-2 N-[4-(7-acetylamino-3-pyridin-3-yl-4,5-dihydro-pyrazolo[4,3-g]benzothiazol-1-yl)-3-fluorophenyl]-3-chloropropionamide

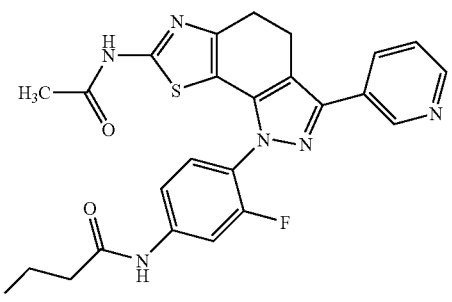

A suspension of III-1 (1.5 g, w=0.75, 2.7 mmol) in 12 mL NMP is combined with 0.5 mL diisopropylethylamine and stirred for 5 min at RT. After the addition of 0.44 mL 3-chloropropionyl chloride the mixture is stirred for 1 h at RT, then combined with water and extracted with dichloromethane. The combined organic phases are dried on magnesium sulphate, filtered and evaporated down. After purification by RP-chromatography (gradient: 5% acetonitrile/water→98% acetonitrile/water; 35 min) the fractions containing the product are lyophilised. Yield: 624 mg.

IV-3 2-chloroethyl[4-(7-acetylamino-3-pyridin-3-yl-4,5-dihydro-pyrazolo[4,3-g]benzothiazol-1-yl)-3-fluorophenyl]-carbamidate

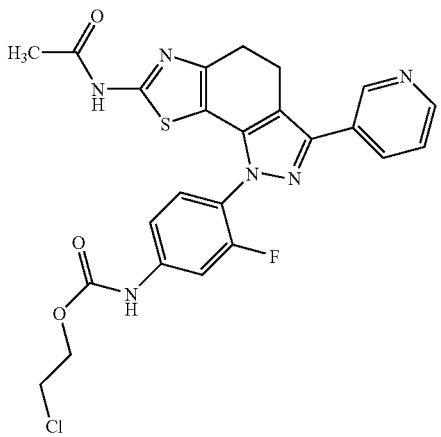

A suspension of III-1 (60 mg, 0.14 mmol) in 3 mL NMP is combined with 80 μL diisopropylethylamine and stirred for 5 min at RT. After the addition of 65 μL of 2-chloroethylchloroformate the mixture is stirred for 1 h at RT, then combined with DMF. After purification by RP-chromatography (gradient: 5% acetonitrile/water→70% acetonitrile/water; 40 min) the fractions containing the product are lyophilised. Yield: 12 mg.

IV-4 N-[4-(7-acetylamino-3-pyridin-3-yl-4,5-dihydropyrazolo[4,3-g]benzothiazol-1-yl)-3-fluorophenyl]-2-chloropropionamide

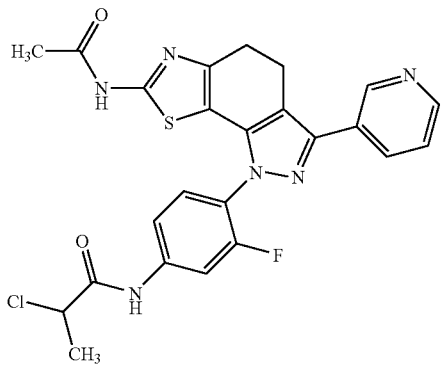

A suspension of III-1 (1.1 g, 2.6 mmol) in 10 mL NMP is combined with 0.9 mL diisopropylethylamine and stirred for 5 min at RT. After the addition of 0.5 mL of 2-chloropropionyl chloride the mixture is stirred for 1 h at RT, then combined with DMF. After purification by RP-chromatography (gradient: 5% acetonitrile/water→70% acetonitrile/water; 40 min) the fractions containing the product are lyophilised. Yield: 382 mg.

Analytical Methods

Method AM1:

HPLC: Agilent 1100 Series; MS: 1100 Series LC/MSD (API-ES (+/−3000V, Quadrupole, G1946D); Mode: Scan pos 100-1000, neg 100-1000

| column: | Waters; Part No. 186000594; XTerra MS C18 2.5 μm; 2.1 × 50 mm column | |
|---|---|---|
| solvent: | A: $H_2O$ desalinated with the addition of 0.1% formic acid B: acetonitrile HPLC grade with the addition of 0.1% formic acid | |
| detection: | peakwide >0.1 min (2 s); 190-450 nm UV 254 nm (bandwide 8, reference off) UV 230 nm (bandwide 8, reference off) | |
| injection: | 1 μL standard injection | |
| flow: | 0.6 mL/min | |
| column temperature: | 35° C. | |
| pump gradient: | 0.0-0.5 min | 5% B |
| | 0.5-1.5 min | 5%->50% B |
| | 1.5-4.0 min | 50%->95% B |
| | 4.0-6.0 min | 95% B |
| | 6.0-6.5 min | 95%->5% B |
| | 1.5 min post run | 5% B |

Method AM2

HPLC: Agilent Series 1100 (G1379A/G1310A converted to G1311A/G1313A/G1316A/G1948D/G1315B/G1946D) Mode: Scan pos 100-1000, neg 100-1000

| column: | Agilent Zorbax SB-C8, 2.1 × 50 mm, 3.5 μm | |
|---|---|---|
| solvent: | A: $H_2O$ desalinated with the addition of 0.1% formic acid B: acetonitrile HPLC grade with the addition of 0.1% formic acid | |
| detection: | peakwide >0.1 min (2 s); 190-450 nm UV 254 nm (bandwide 8, reference off) UV 230 nm (bandwide 8, reference off) | |
| injection: | 2.5 μL standard injection | |
| flow: | 0.6 mL/min | |
| column temperature: | 35° C. | |
| pump gradient: | 0-3.0 min | 10%->90% B |
| | 3.0-4.0 min | 90% B |
| | 4.0-5.0 min | 90%->10% B |

Method AM3

HPLC: Agilent Series 1100 (G1312A/G1315A/G1316A/G1367A) Agilent MSD SL ESI

Mode: Scan pos 150-750

| column: | Agilent Zorbax SB-C8, 2.1 × 50 mm, 3.5 μm |
|---|---|
| solvent: | A: $H_2O$ desalinated with the addition of 0.1% formic acid B: acetonitrile HPLC grade with the addition of 0.1% formic acid |
| detection: | peakwidth >0.01 min (0.2 s); 190-450 nm UV 254 nm (bandwide 16, reference off) UV 230 nm (bandwide 8, reference off) UV 214 nm (bandwide 8, reference off) |
| injection: | 3.0 μL overlap injection |
| flow: | 1.1 mL/min |
| column temperature: | 45° C. |
| pump gradient: | 0-1.75 min 15% ≧ 95% B 1.75-1.90 min 95% B 1.90-1.92 min 950% ≧ 15% B |

Method AM4

| HPLC: | Agilent 1100 Series | |
|---|---|---|
| MS: | Agilent LC/MSD SL | (LCMS 1: 1100 series LC/MSD) |
| column: | Waters, Xterra MS C18, 2.5 μm, 2.1 × 30 mm, Part. No. 186000592 | |
| solvent | A: $H_2O$ desalinated with the addition of 0.1% formic acid B: acetonitrile HPLC grade with the addition of 0.1% formic acid | |
| detection: | MS: Positive and negative Mass range: 120-900 m/z Fragmentor: 120 | |
| Gain EMV: | 1 | |
| Threshold: | 150 | |
| Stepsize: | 0.25 | |
| | UV: 254 nm | |
| Bandwide: | 1 | (LCMS1: 2) |
| Reference: Spectrum: | off | |
| | Range: 250-400 nm Rangestep: 1.00 nm Threshold: 4.00 mAU | |
| Peakwidth: | <0.01 min | (LCMS1: >0.05 min) |
| Slit: | 1 nm | (LCMS1: 2 nm) |

-continued

| injection: | 5 µL | |
|---|---|---|
| flow: | 1.10 mL/min | |
| column temperature: | 40° C. | |
| gradient: | 0.00 min | 5% B |
| | 0.00-2.50 min | 5% ≧ 95% B |
| | 2.50-2.80 min | 95% B |
| | 2.81-3.10 min | 95% ≧ 5% B |

Method AM5

| HPLC: | Agilent 1100 Series | |
|---|---|---|
| MS: | Agilent LC/MSD SL | (LCMS1: 1100 series LC/MSD) |
| Column: | Phenomenex, Synergi Polar RP 80A, 4 µm, 2 × 30 mm, Part. No. 00A-4336-B0 | |
| Solvent: | A: H₂O (Millipore purified purest water) with the addition of 0.1% formic acid B: acetonitrile (HPLC grade) | |
| Detection: | MS: Positive and negative Mass range: 120-900 m/z Fragmentor: 120 | |
| Gain EMV: 1 | | |
| Threshold: | 150 | |
| Stepsize: | 0.25 | |
| UV: | 254 nm | |
| Bandwide: | 1 | (LCMS1: 2) |
| Reference: | off | |
| Spectrum: | Range: 250-400 nm Range step: 1.00 nm Threshold: 4.00 mAU | |
| | Peakwidth: <0.01 min | (LCMS1: >0.05 min) |
| | Slit: 1 nm | (LCMS1: 2 nm) |
| Injection: | Inj. Vol.: 5 µL | |
| Inj. mode: | Needle wash | |
| Separation: | Flow: 1.10 mL/min Column temp.: 40° C. | |
| | gradient: 0.00 min | 5% solvent B |
| | 0.00-2.50 min | 5% ≧ 95% solvent B |
| | 2.50-2.80 min | 95% solvent B |
| | 2.81-3.10 min | 95% ≧ 5% solvent B |

Method AM6

| HPLC: | Waters Alliance 2695 | |
|---|---|---|
| column: | Waters, Xterra MS C18, 2.5 µm, 4.6 × 30 mm, Part. No. 186000600 | |
| solvent | A: H₂O desalinated with the addition of 0.1% formic acid B: acetonitrile HPLC grade with the addition of 0.08% formic acid | |
| flow: | 1 mL/min | |
| column temperature: | 25° C. | |
| gradient: | 0.00 min | 5% B |
| | 0.00-3.10 min | 5% ≧ 98% B |
| | 3.10-4.50 min | 98% B |
| | 4.50-5.00 min | 98% ≧ 5% B |

Abbreviations Used

DC thin layer chromatography
DMF N,N-dimethylformamide
DMSO dimethylsulphoxide
h hour
HATU O-(7-azabenzotriazol-1-yl)-N,N,N',N'-tetramethyluronium hexafluorophosphate
HPLC high performance liquid chromatography
conc. concentrated
M molar
min minute
ML milliliter
MS mass spectrometry
N normal
NaOH sodium hydroxide
NMR nuclear resonance spectroscopy
NMP N-methylpyrrolidinone
Rf retention factor
RP reversed phase
RT ambient temperature
Rt retention time
m.p melting point
tert tertiary
THF tetrahydrofuran
w mass content Examples 1.1-1.7

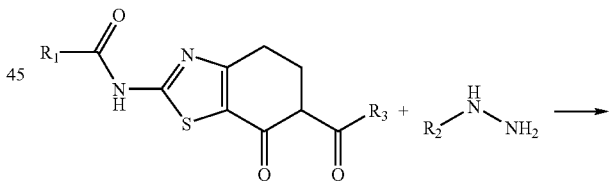

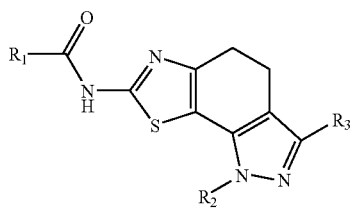

Examples 1.1-1.7 are prepared analogously to synthesis I-1.

| # | educt | structure | mass [M + 1]⁺ | HPLC Rt [min] |
|---|---|---|---|---|
| 1.1 | Z-1 | 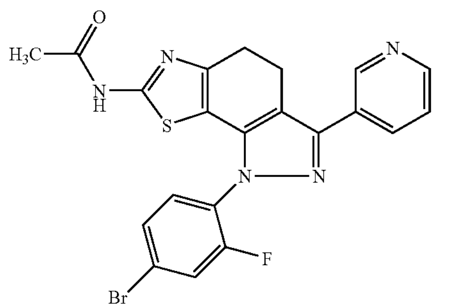 | 484/486 | 1.75 |
| 1.2 | Z-1 H-5 | 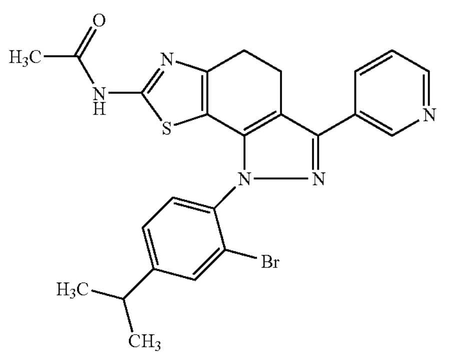 | 508/510 | 1.89 |
| 1.3 | Z-1 H-6 | 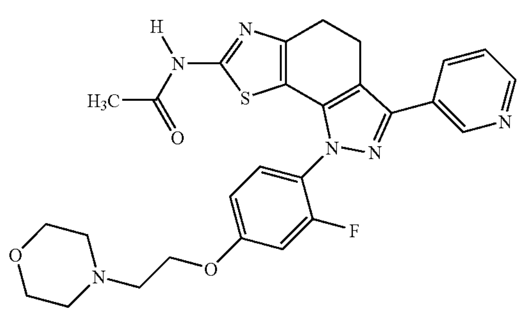 | 535 | 1.31 |
| 1.4 | Z-1 | 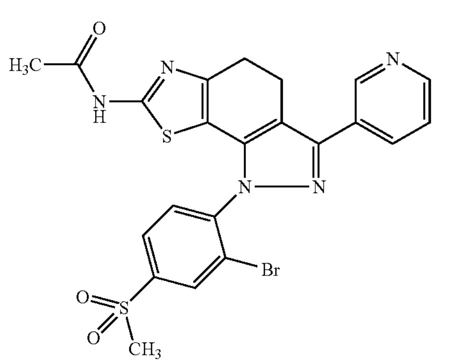 | 544/546 | 1.56 |

| # | educt | structure | mass [M + 1]⁺ | HPLC Rt [min] |
|---|---|---|---|---|
| 1.5 | Z-1 | 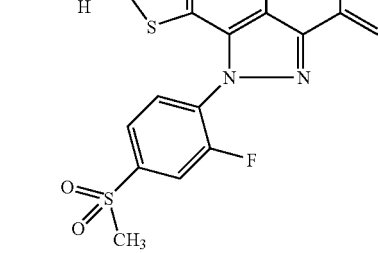 | 484 | 1.53 |
| 1.6 | Z-1<br>H-4 | 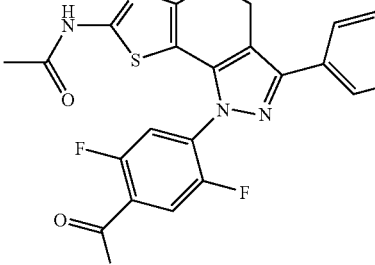 | 482 | 1.75 |
| 1.7 | Z-1<br>H-7 | 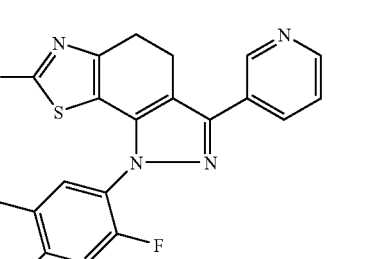 | 449 | 1.64 |

Reaction of the Carboxylic Acids With Amines

Synthesis Method A

A solution of a carboxylic acid (0.1 mmol) in 5 mL dichloromethane or DMF is combined with O-benzotriazol-1-yl-N,N,N',N'-tetramethyluronium tetrafluoroborate (0.15 mmol) and diisopropylethylamine (0.3 mmol) and stirred for 15 min at RT. Then the corresponding amine (0.1 mmol) is added and the mixture is stirred at RT until the reaction is complete. The reaction mixture is combined with aqueous 5% potassium carbonate solution and extracted with dichloromethane. The combined organic phases are dried and evaporated down in vacuo. The residue is crystallised from petroleum ether or purified by chromatography.

Synthesis Method B

A solution of a carboxylic acid (0.35 mmol) in 5 mL DMF (or dichloromethane, or THF) is combined with HATU (0.55 mmol) and diisopropylethylamine (1.8 mmol) and stirred for 15 min at RT. After the addition of the corresponding amine (0.39 mmol) the mixture is stirred for 15 h at RT, combined with aqueous 5% potassium carbonate solution and extracted with dichloromethane. The combined organic phases are dried and evaporated down in vacuo. The residue is purified by chromatography.

Synthesis Method C

The synthesis is carried out analogously to Synthesis method A, except that triethylamine is used instead of diisopropylethylamine.

Synthesis Method D

The synthesis is carried out analogously to Synthesis method B, except that triethylamine is used instead of diisopropylethylamine.

Examples 2.1-2.58
| # | educt | structure | mass [M + 1]+ | HPLC [min] |
|---|---|---|---|---|
| 2.1 | II-2 | 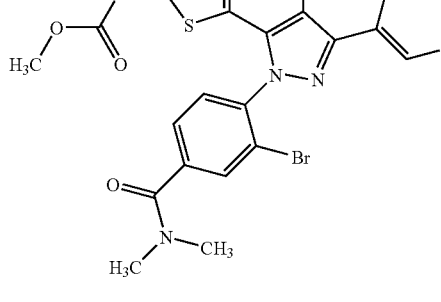 | 553/555 | 1.56 |
| 2.2 | II-1 | 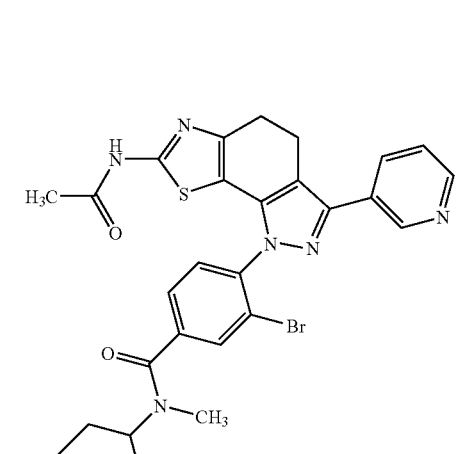 | 620/622 | 1.28 |
| 2.3 | II-1 | 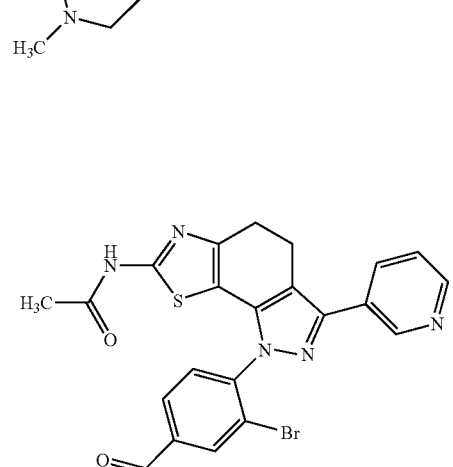 | 503/595 | 1.52 |

-continued

| # | educt | structure | mass [M + 1]+ | HPLC [min] |
|---|-------|-----------|---------------|------------|
| 2.5 | II-1 | 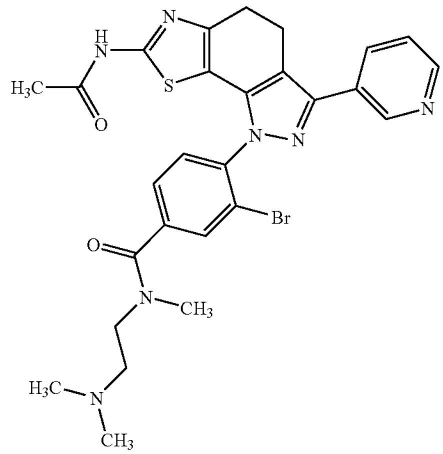 | 594/596 | 0.12 |
| 2.6 | II-1 | 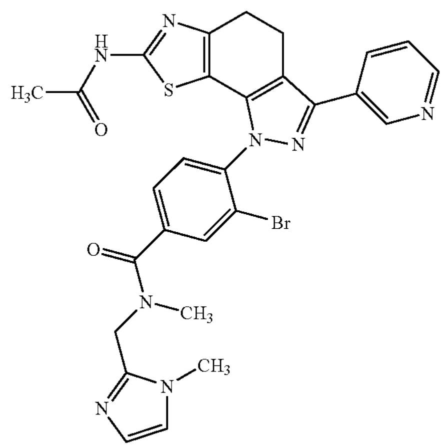 | 617/619 | 0.12 |
| 2.7 | II-1 | 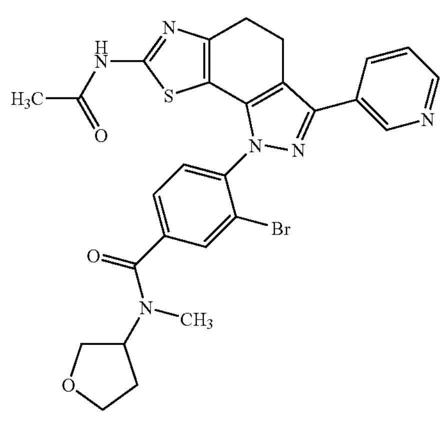 | 593/595 | 1.57 |

-continued
| # | educt | structure | mass [M + 1]+ | HPLC [min] |
|---|---|---|---|---|
| 2.8 | II-1 | 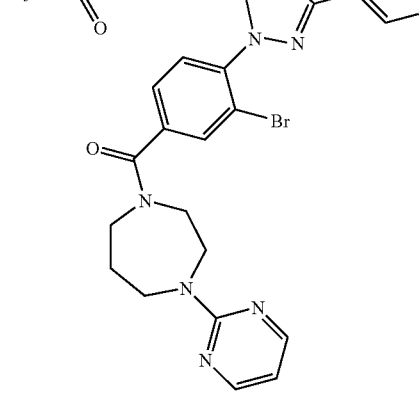 | 670/672 | 1.64 |
| 2.9 | II-1 | 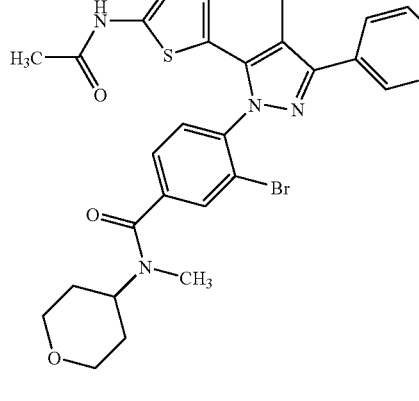 | 607/609 | 1.6 |
| 2.10 | II-1 | 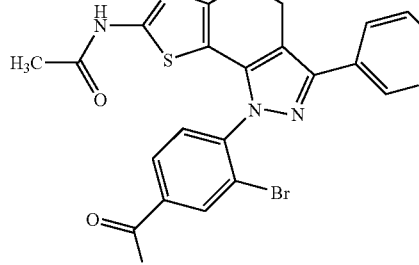 | 567/569 | 0.14 |

-continued

| # | educt | structure | mass [M + 1]⁺ | HPLC [min] |
|---|---|---|---|---|
| 2.11 | II-1 | 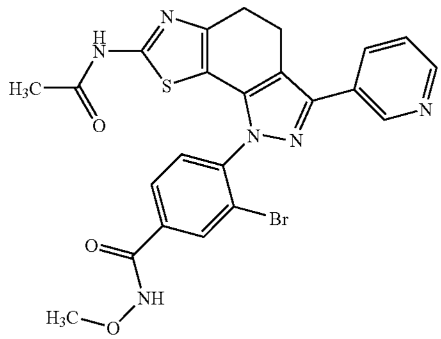 | 539/541 | 1.48 |
| 2.12 | II-1 | 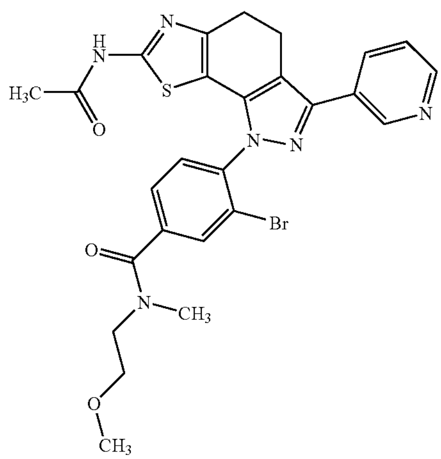 | 581/583 | 1.56 |
| 2.13 | II-1 | 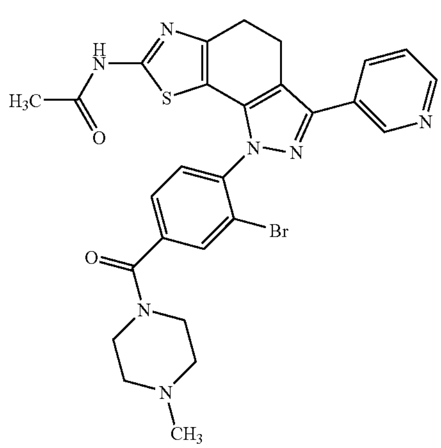 | 592/594 | 0.12 |

-continued

| # | educt | structure | mass [M + 1]+ | HPLC [min] |
|---|---|---|---|---|
| 2.14 | II-1 | 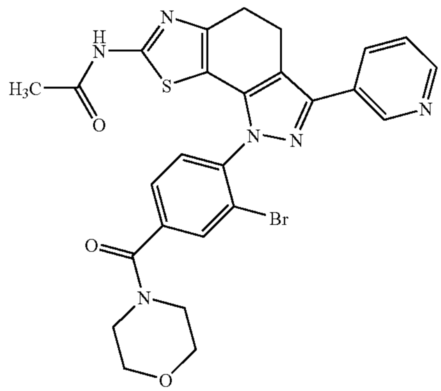 | 579/581 | 1.54 |
| 2.15 | II-1 | 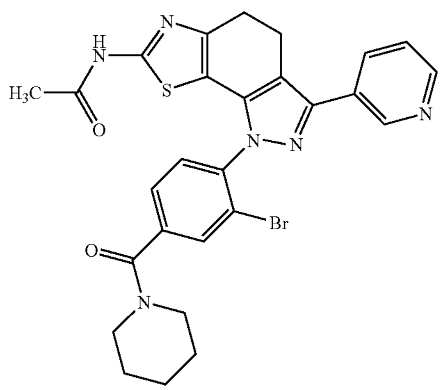 | 577/579 | 1.72 |
| 2.16 | II-1 | 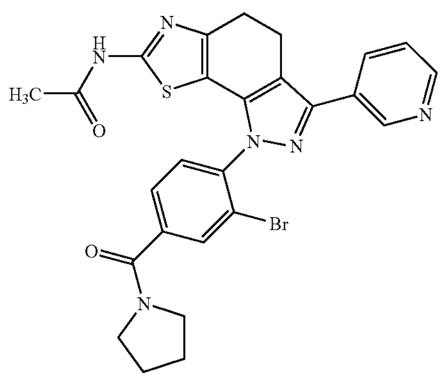 | 563/565 | 1.61 |
| 2.17 | II-1 | 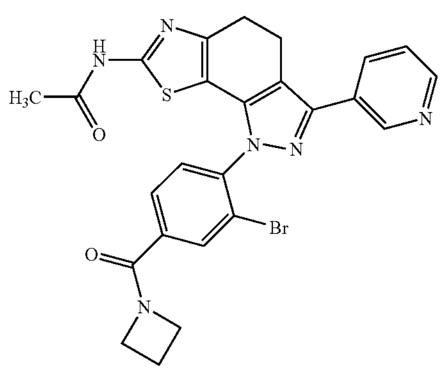 | 549/551 | 1.54 |

-continued

| # | educt | structure | mass [M + 1]+ | HPLC [min] |
|---|---|---|---|---|
| 2.18 | II-1 | 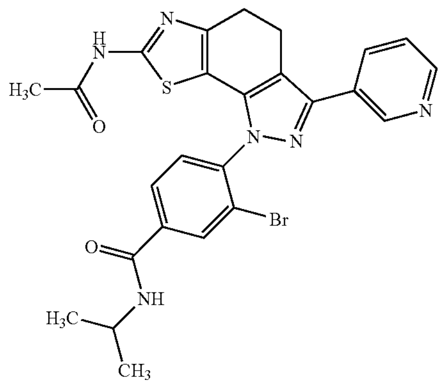 | 551/553 | 1.64 |
| 2.19 | II-1 | 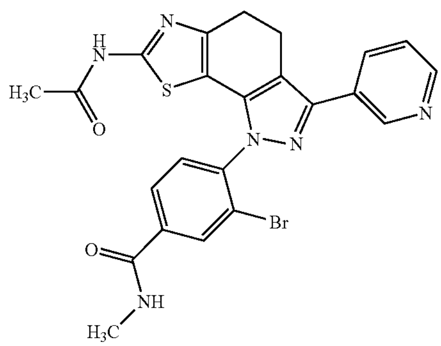 | 523/525 | 1.41 |
| 2.20 | II-1 | 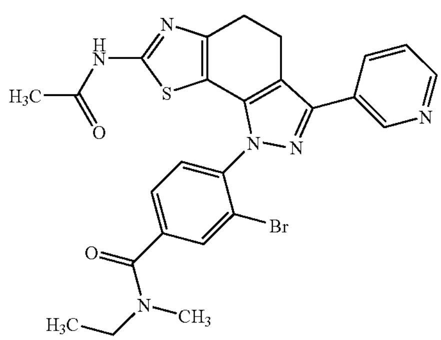 | 551/553 | 1.58 |
| 2.21 | II-1 | 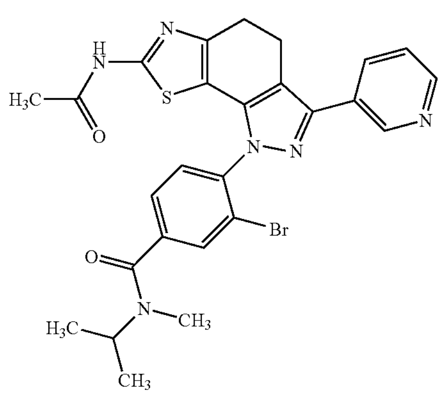 | 565/567 | 1.7 |

-continued
| # | educt | structure | mass [M + 1]⁺ | HPLC [min] |
|---|---|---|---|---|
| 2.22 | II-1 | 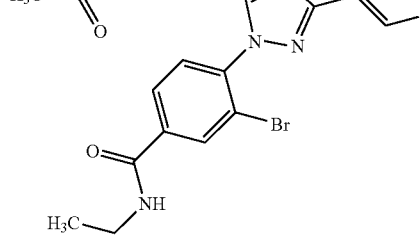 | 537/539 | 1.54 |
| 2.23 | II-1 | 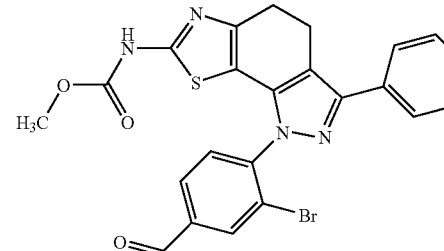 | 537/539 | 1.5 |
| 2.24 | II-1 | 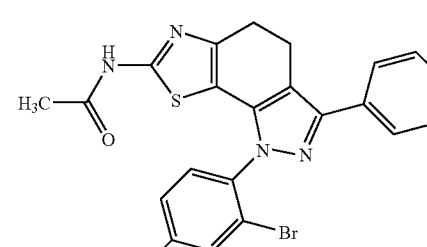 | 606/608 | 1.28 |
| 2.25 | II-1 | 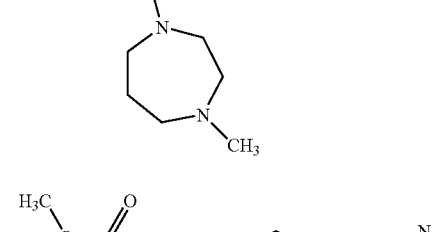 | 507 | 1.62 |

-continued
| # | educt | structure | mass [M + 1]+ | HPLC [min] |
|---|---|---|---|---|
| 2.26 | II-3 | 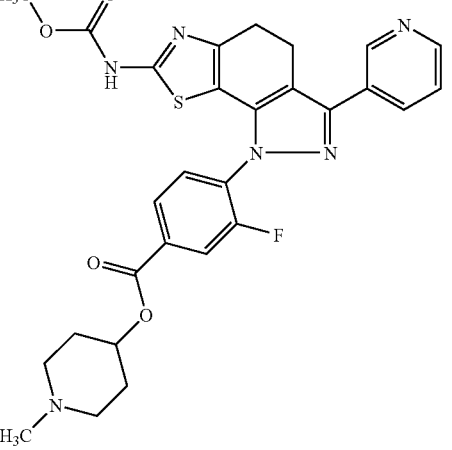 | 563 | 1.4 |
| 2.27 | II-3 | 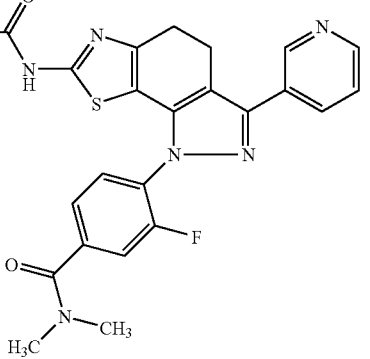 | 593 | 1.56 |
| 2.28 | II-3 | 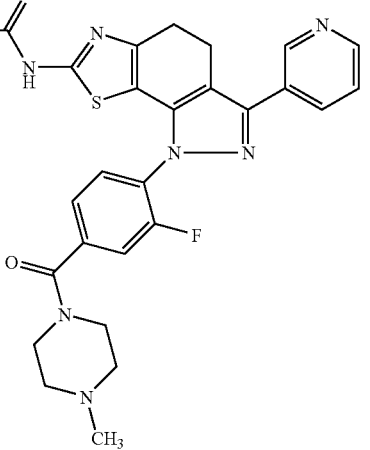 | 548 | 1.31 |

-continued
| # | educt | structure | mass [M + 1]⁺ | HPLC [min] |
|---|---|---|---|---|
| 2.29 | II-3 | 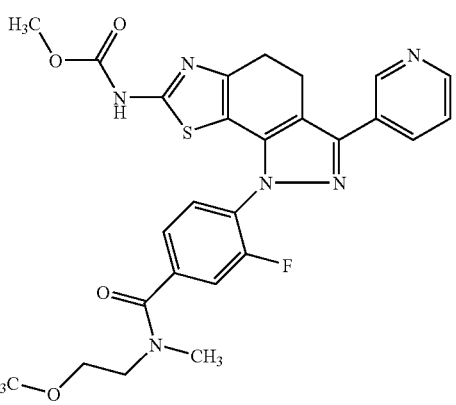 | 537 | 1.6 |
| 2.30 | II-3 | 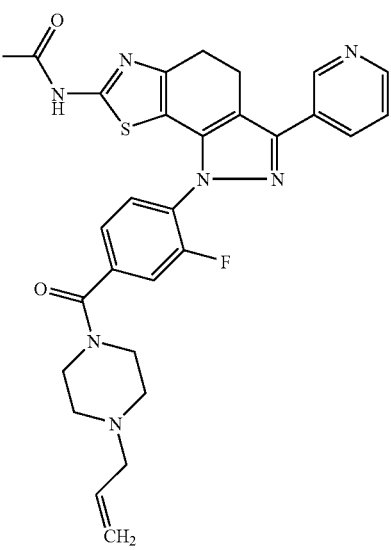 | 574 | 1.41 |
| 2.31 | I-5 | 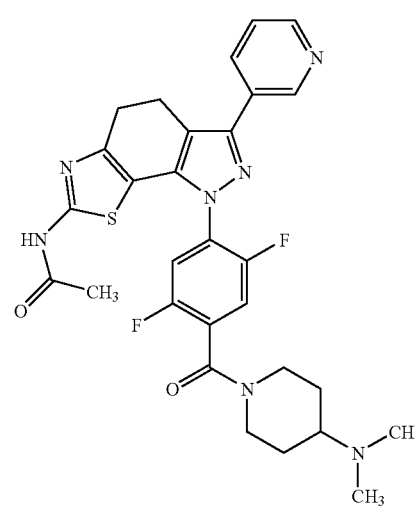 | 578 | 1.34 |

-continued

| # | educt | structure | mass [M + 1]⁺ | HPLC [min] |
|---|---|---|---|---|
| 2.32 | I-5 | 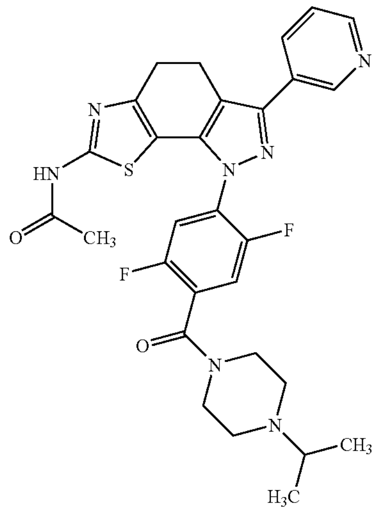 | 578 | 1.39 |
| 2.33 | I-5 | 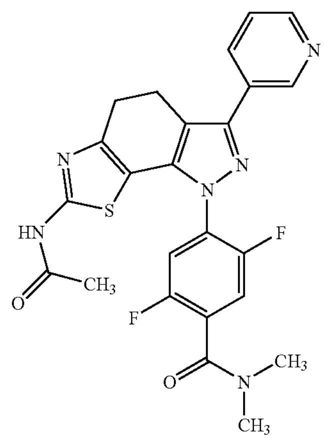 | 495 | 1.57 |
| 2.34 | I-5 | 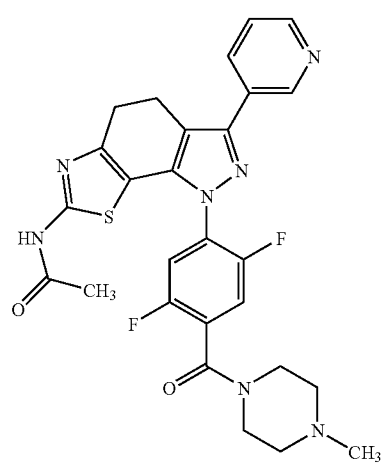 | 550 | 1.32 |

-continued

| # | educt | structure | mass [M + 1]+ | HPLC [min] |
|---|---|---|---|---|
| 2.35 | II-4 | 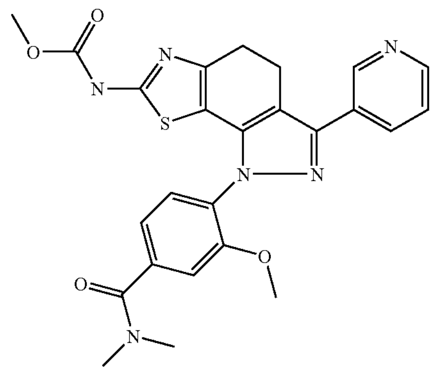 | 505 | 1.47 |
| 2.36 | II-4 | 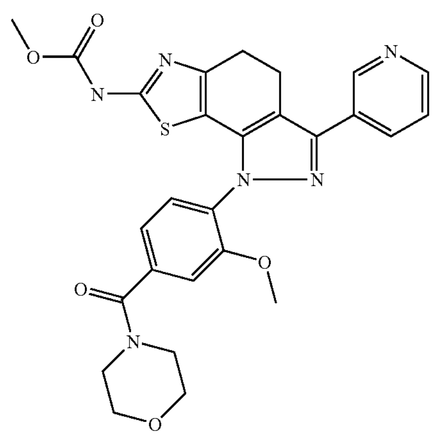 | 547 | 1.49 |
| 2.37 | II-4 | 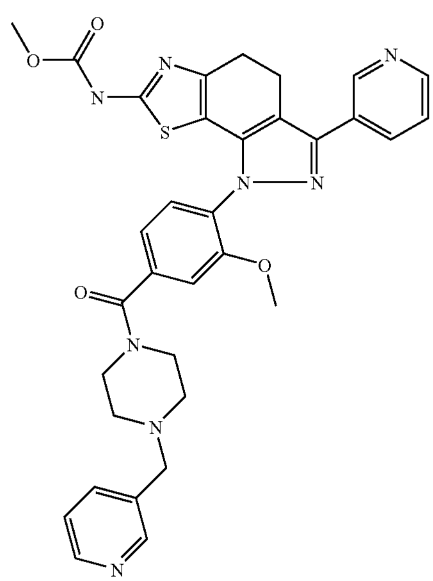 | 637 | |

| # | educt | structure | mass [M + 1]⁺ | HPLC [min] |
|---|---|---|---|---|
| 2.38 | II-1 | 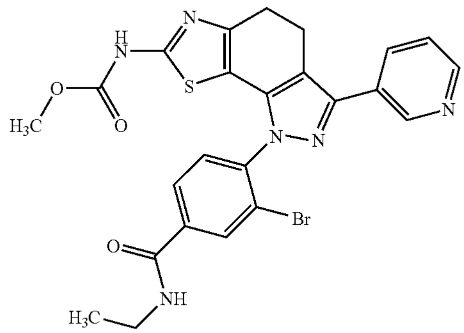 | 553/555 | 1.62 |
| 2.39 | II-1 | 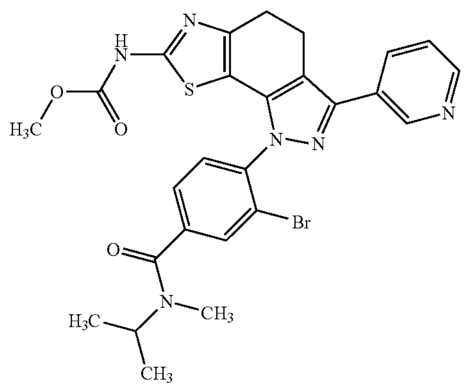 | 581/583 | 1.76 |
| 2.40 | II-1 | 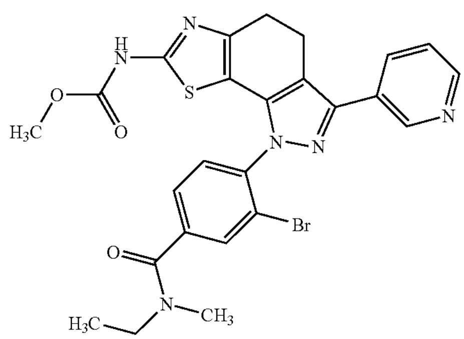 | 567/569 | 1.66 |
| 2.41 | II-1 | 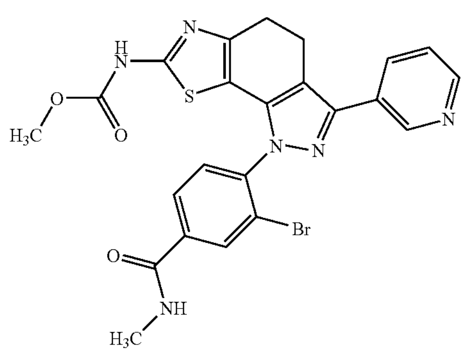 | 539/541 | 1.53 |

| # | educt | structure | mass [M + 1]⁺ | HPLC [min] |
|---|---|---|---|---|
| 2.42 | II-1 | 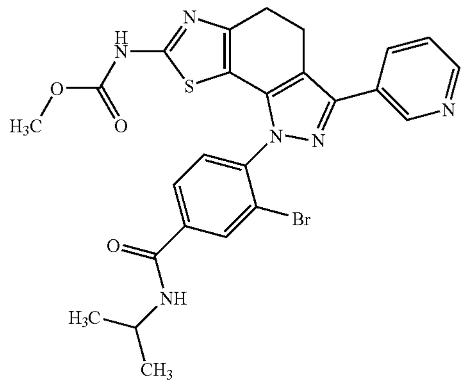 | 567/569 | 1.69 |
| 2.43 | II-1 | 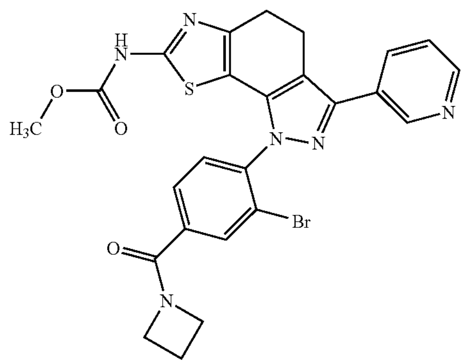 | 565/567 | 1.62 |
| 2.44 | II-1 | 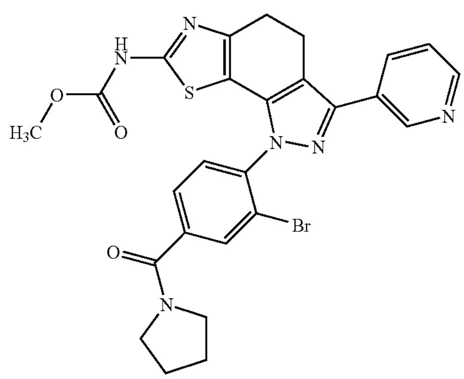 | 579/581 | 1.67 |
| 2.45 | II-1 | 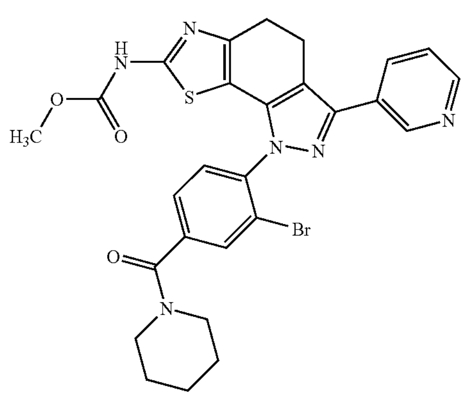 | 583/595 | 1.79 |

-continued

| # | educt | structure | mass [M + 1]+ | HPLC [min] |
|---|---|---|---|---|
| 2.46 | II-1 | 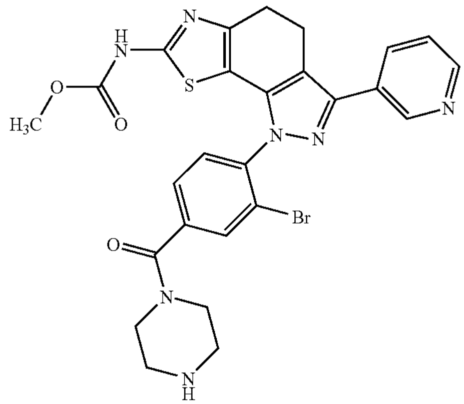 | 594/596 | 1.29 |
| 2.47 | II-1 | 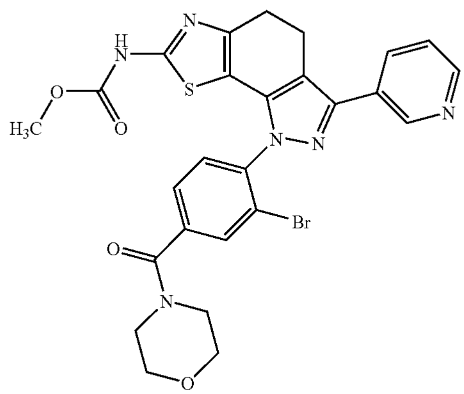 | 595/597 | 1.62 |
| 2.48 | II-1 | 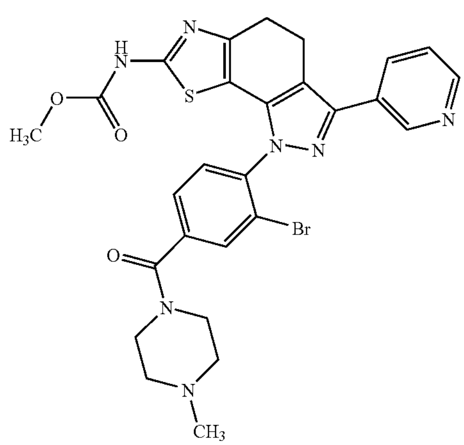 | 608/610 | 1.02 |

-continued

| # | educt | structure | mass [M + 1]+ | HPLC [min] |
|---|---|---|---|---|
| 2.49 | II-1 | 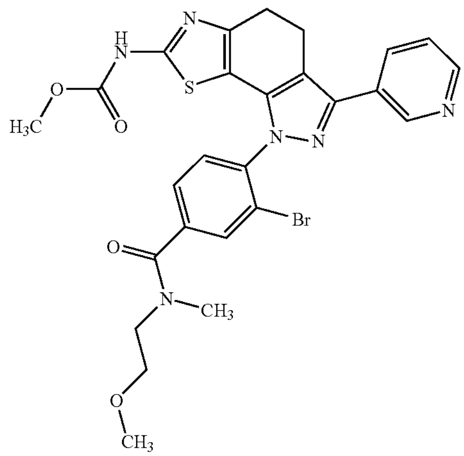 | 597/599 | 1.64 |
| 2.50 | II-1 | 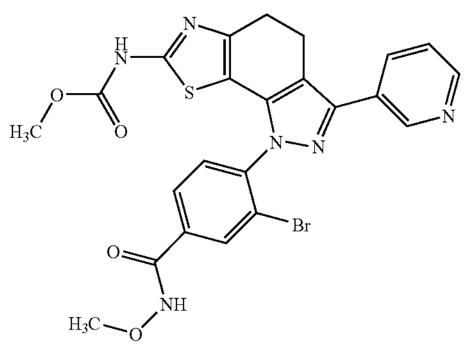 | 555/557 | 1.5 |
| 2.51 | II-1 | 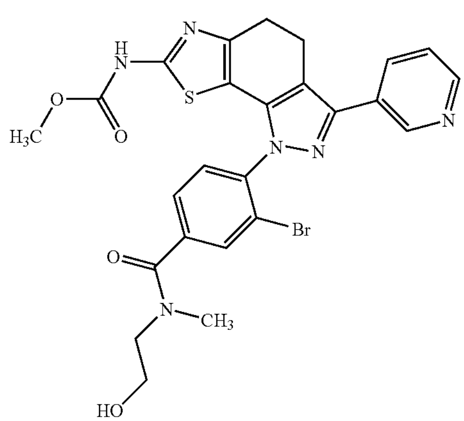 | 583/585 | 1.48 |

-continued
| # | educt | structure | mass [M + 1]+ | HPLC [min] |
|---|---|---|---|---|
| 2.52 | II-1 | 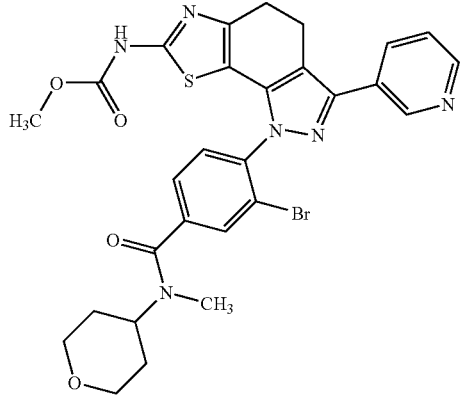 | 623/625 | 1.66 |
| 2.53 | II-1 | 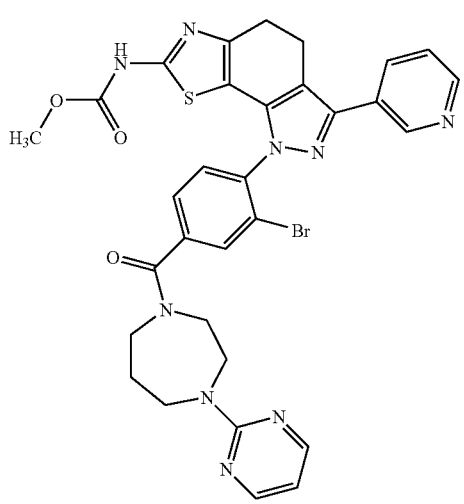 | 686/688 | 1.72 |
| 2.54 | II-1 | 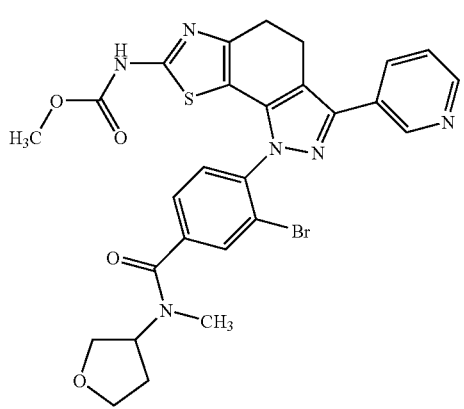 | 609/611 | 1.64 |

-continued

| # | educt | structure | mass [M + 1]+ | HPLC [min] |
|---|---|---|---|---|
| 2.55 | II-1 | 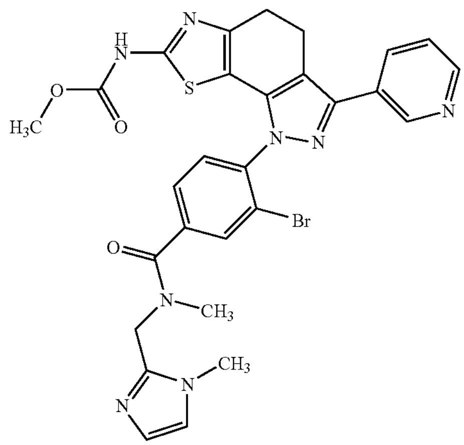 | 633/635 | |
| 2.56 | II-1 | 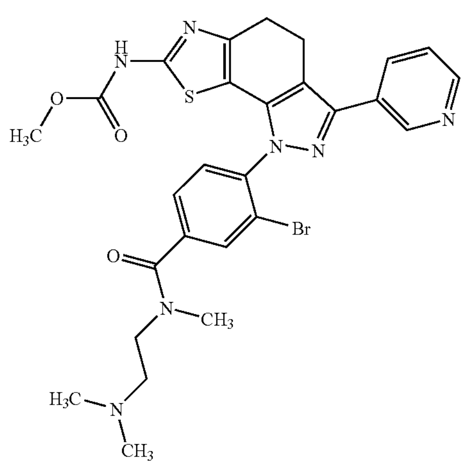 | 610/612 | 1.3 |

| # | educt | structure | mass [M + 1]⁺ | HPLC [min] |
|---|---|---|---|---|
| 2.57 | II-1 | 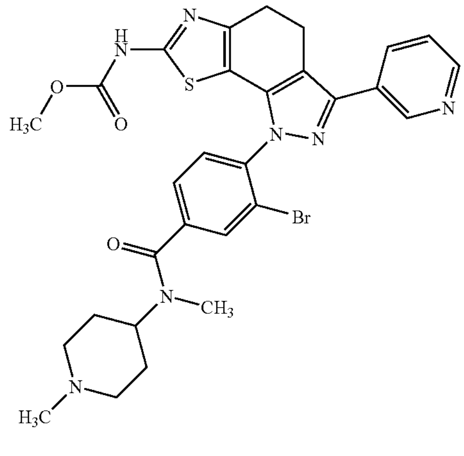 | 636/638 | |
| 2.58 | II-1 | 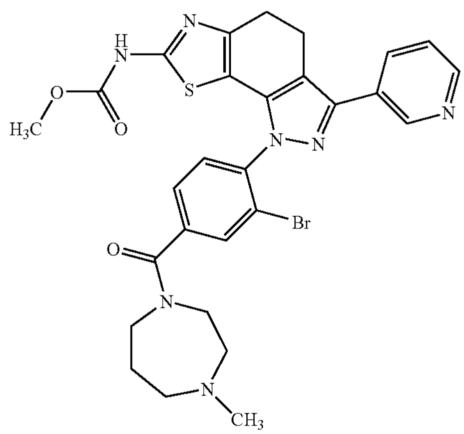 | 622/624 | |

Reaction of the Prepared Amine

Synthesis Method E—Reaction With Sulphonic Acid Chlorides

A solution of 0.2 mmol amine in 3 mL pyridine is combined with 0.5 mmol sulphonic acid chloride and stirred for 15 h at RT. The reaction mixture is evaporated down and the residue is purified by chromatography.

Synthesis Method F—Reaction With Carboxylic Acids

A solution of the carboxylic acid (0.16 mmol) in 1.3 mL DMF is combined with HATU (0.55 mmol) and diisopropylethylamine (1.8 mmol) and stirred for 1 h at RT. After the addition of a solution of 0.1 mmol of the corresponding amine in DMF stirring is continued for a further 15 h at RT. Then the reaction mixture is filtered, evaporated down and the residue is purified by chromatography.

Synthesis Method G—Reaction With Carboxylic Acid Chlorides

The carboxylic acid chlorides used are either commercially obtainable or are obtained by reacting the corresponding carboxylic acid (0.6 mmol) with 2 mL thionyl chloride.

a) A solution of 0.2 mmol amine in 3 mL pyridine is combined with 0.5 mmol carboxylic acid chloride and stirred for 15 h at RT. The reaction mixture is evaporated down and the residue is purified by chromatography.

b) The synthesis is carried out analogously to Synthesis method a) except that 3 mL DMF and 45 µL triethylamine are used instead of pyridine.

c) The synthesis is carried out analogously to Synthesis method a) except that 2 mL NMP and 80 µL diisopropylethylamine are used instead of pyridine.

Synthesis Method H—Reaction With Chloroformates

The chloroformates used are either commercially obtainable or are prepared in situ by reacting the corresponding alcohol (1.4 mmol) with equivalents of phosgene (20% in toluene; 1.2 mmol) in 1 mL THF. The reaction solution is used directly without any further working up.

A solution of 0.14 mmol amine in 2 mL NMP is combined with 80 µL diisopropylethylamine and stirred for 5 min. Then the carbamoylchloride is added in four batches of 10 mg and the mixture is stirred for 14 h. The reaction mixture is directly purified by chromatography on RP-silica gel.

Examples 3.1-3.23

| # | educt | structure | mass [M + 1]+ | HPLC Rt [min] |
|---|---|---|---|---|
| 3.1 | III-4 | 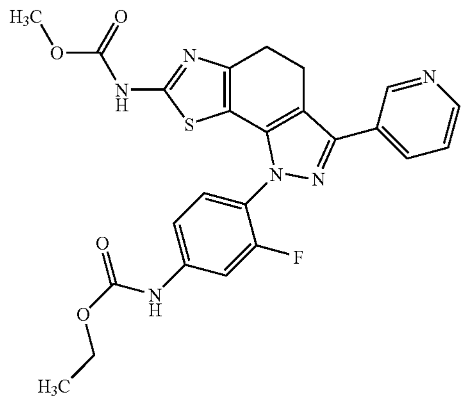 | 509 | 1.71 |
| 3.2 | III-1 | 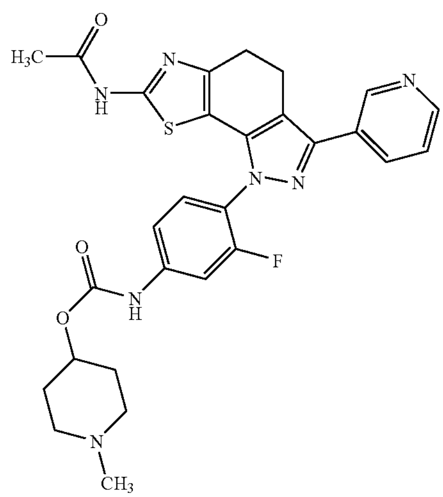 | 562 | 1.39 |
| 3.3 | III-1 | 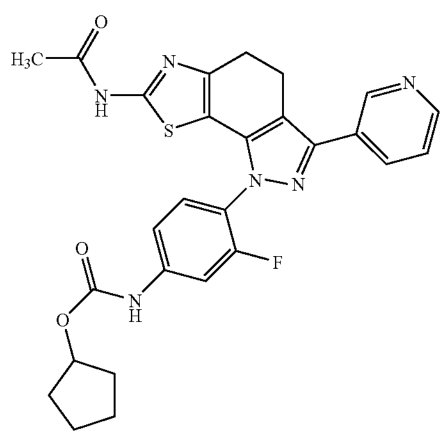 | 533 | 1.88 |

| # | educt | structure | mass [M + 1]+ | HPLC Rt [min] |
|---|---|---|---|---|
| 3.4 | III-1 | 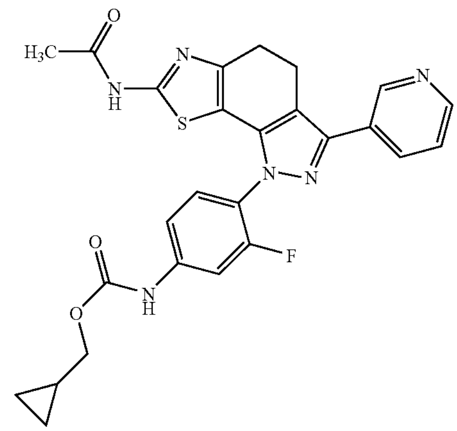 | 519 | 1.78 |
| 3.5 | III-5 | 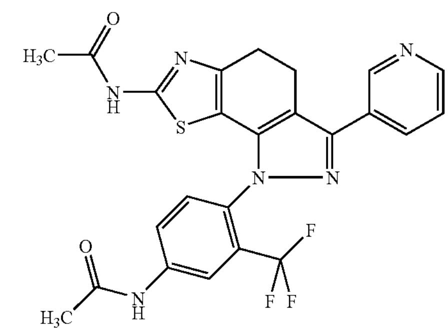 | 513 | 1.52 |
| 3.6 | III-1 | 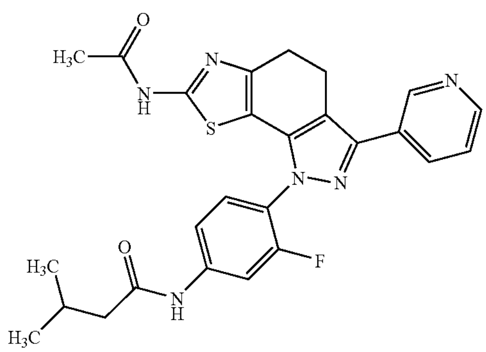 | 505 | 1.75 |
| 3.7 | III-1 | 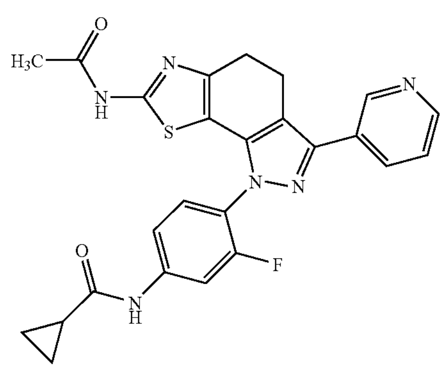 | 489 | 1.61 |

| # | educt | structure | mass [M + 1]+ | HPLC Rt [min] |
|---|---|---|---|---|
| 3.8 | III-1 | 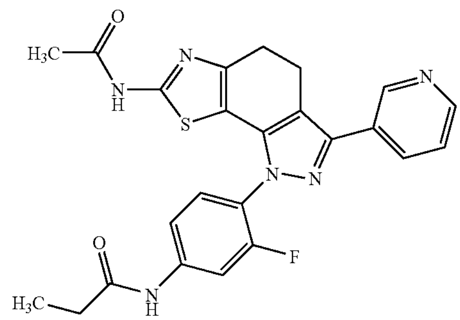 | 477 | 1.55 |
| 3.9 | III-1 | 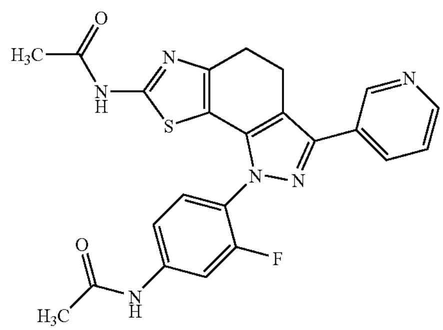 | 463 | 1.46 |
| 3.10 | III-1 | 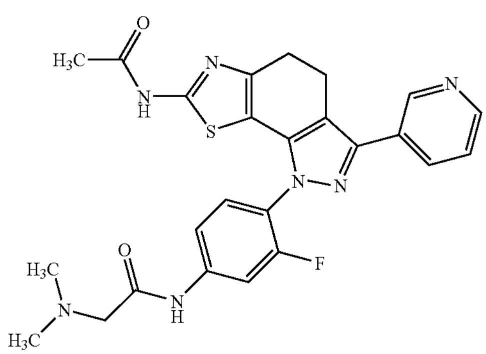 | 506 | 1.3 |
| 3.11 | III-1 | 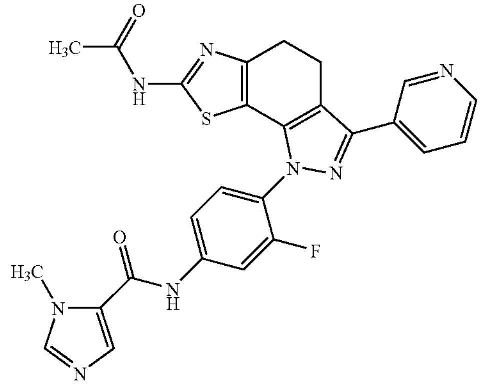 | 529 | 1.43 |

-continued
| # | educt | structure | mass [M + 1]+ | HPLC Rt [min] |
|---|---|---|---|---|
| 3.12 | III-1 | 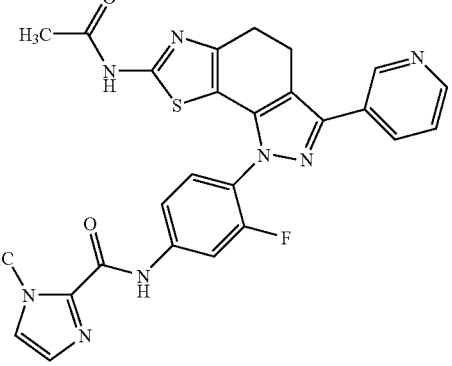 | 529 | 1.66 |
| 3.13 | III-1 | 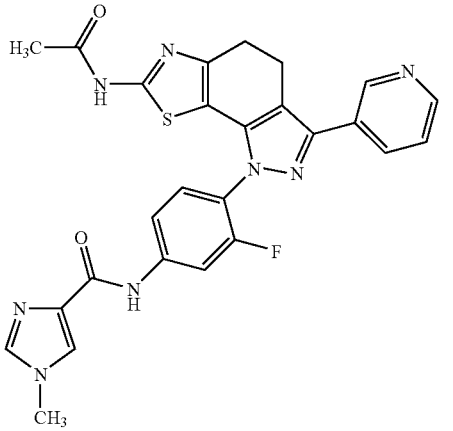 | 529 | 1.44 |
| 3.14 | III-1 | 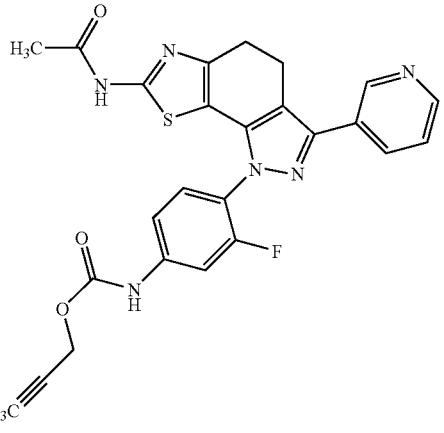 | 503 | 1.66 |

-continued

| # | educt | structure | mass [M + 1]+ | HPLC Rt [min] |
|---|---|---|---|---|
| 3.15 | III-1 | 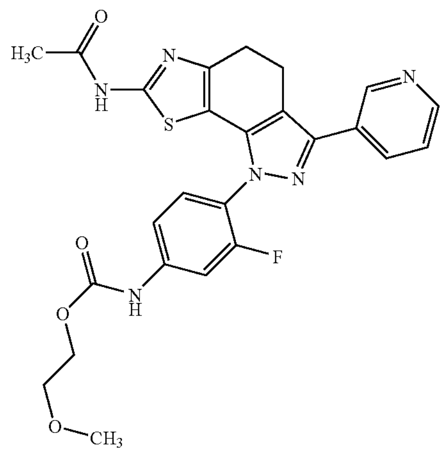 | 523 | 1.6 |
| 3.16 | III-1 | 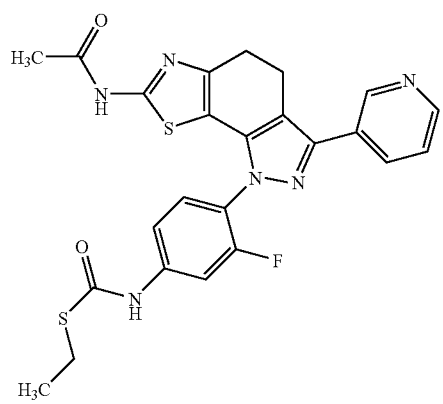 | 509 | 1.78 |
| 3.17 | III-1 | 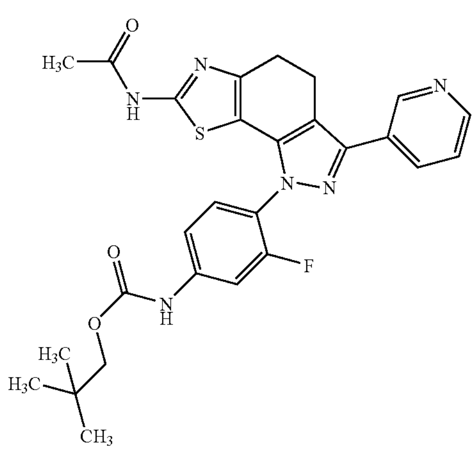 | 535 | 1.96 |

-continued

| # | educt | structure | mass [M + 1]+ | HPLC Rt [min] |
|---|---|---|---|---|
| 3.18 | III-1 | 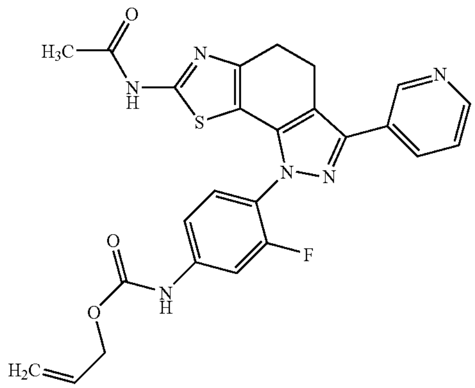 | 505 | 1.73 |
| 3.19 | III-1 | 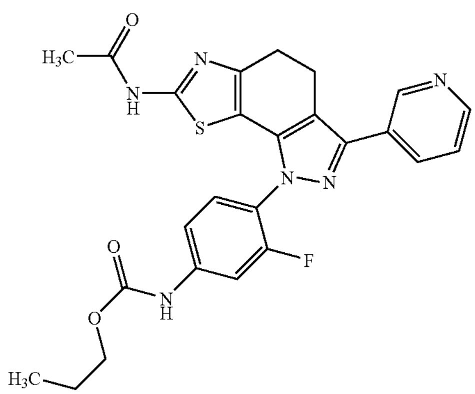 | 507 | 1.77 |
| 3.20 | III-1 | 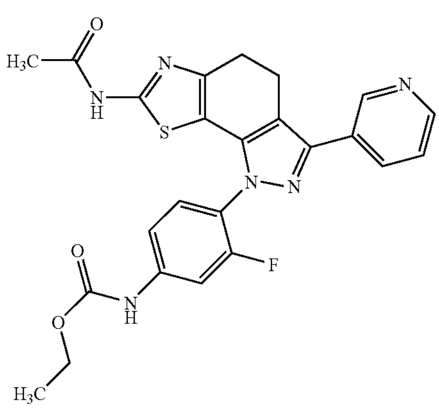 | 493 | 1.66 |

-continued

| # | educt | structure | mass [M + 1]+ | HPLC Rt [min] |
|---|---|---|---|---|
| 3.21 | III-6 | 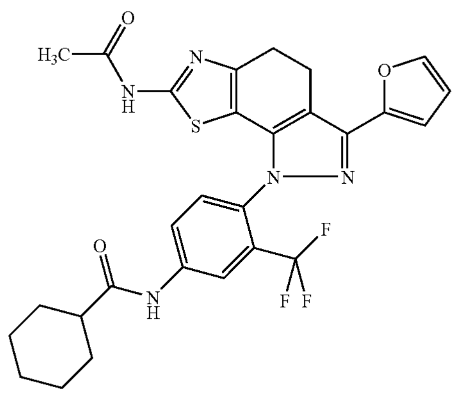 | 570 | 2.33 |
| 3.22 | III-1 | 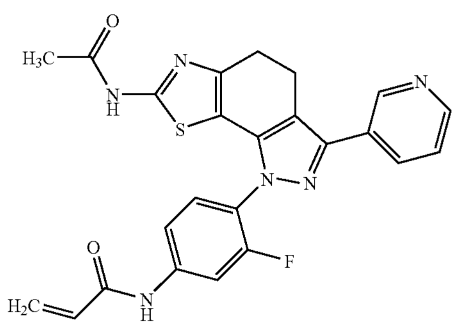 | 475 | 1.56 |
| 3.23 | III-1 | 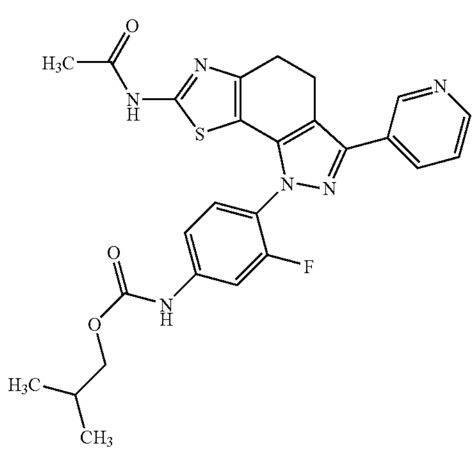 | 521 | 1.88 |

Example 4.1

N-[4-(7-acetylamino-3-pyridin-3-yl-4,5-dihydro-pyrazolo[4,3-g]benzothiazol-1-yl)-3-fluorophenyl]-2-morpholin-4-yl-acetamide

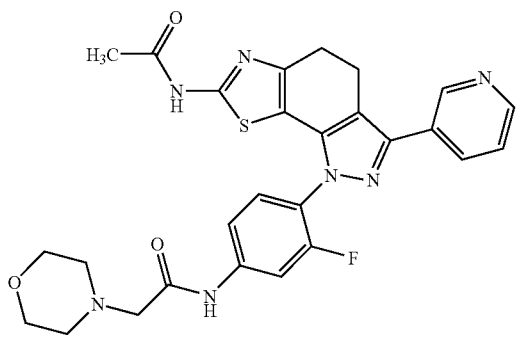

A solution of IV-1 (50 mg, 0.1 mmol) and morpholine (0.1 mL, 1.1 mmol) in 1 mL DMF is stirred for 10 min at 100° C. in the microwave (CEM). Then the reaction mixture is combined with a little DMSO and purified by chromatography on RP-silica gel.

Yield: 33 mg.
HPLC: Rt=1.32 min
[M+1]$^+$=548

Examples 4.2-4.22

Examples 4.2-4.22 are synthesised analogously to Example 4.1:

| # | educt | structure | mass [M + 1]$^+$ | HPLC Rt [min] |
|---|-------|-----------|------------------|---------------|
| 4.2 | IV-1 | 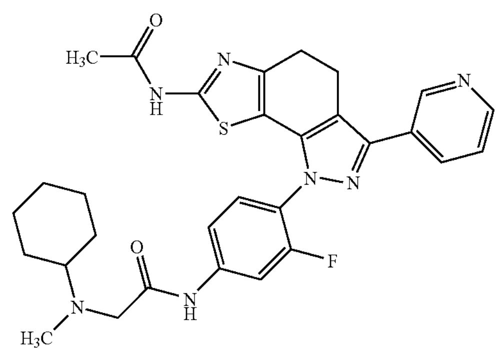 | 574 | 1.41 |
| 4.3 | IV-1 | 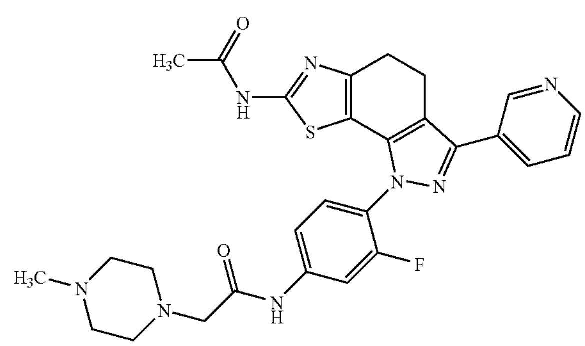 | 561 | 1.33 |

-continued
| # | educt | structure | mass [M + 1]+ | HPLC Rt [min] |
|---|---|---|---|---|
| 4.4 | IV-1 | 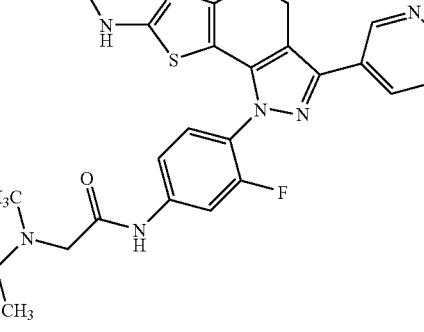 | 534 | 1.35 |
| 4.5 | IV-1 | 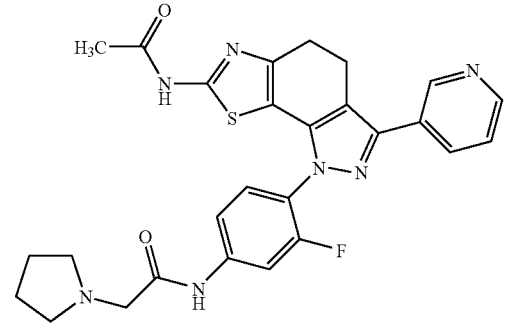 | 532 | 1.36 |
| 4.6 | IV-1 | 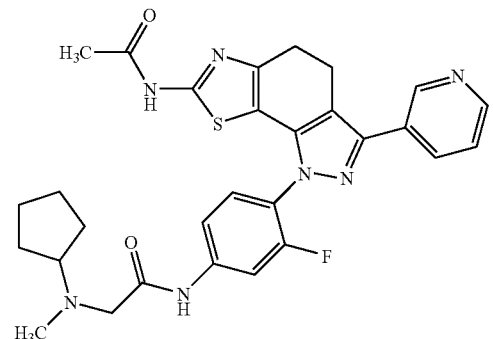 | 560 | 1.43 |
| 4.8* | IV-3 | 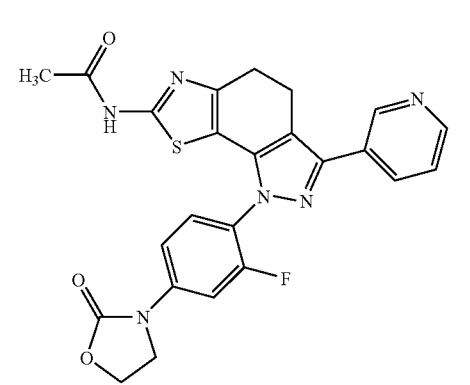 | 491 | 1.44 |

-continued

| # | educt | structure | mass [M + 1]+ | HPLC Rt [min] |
|---|---|---|---|---|
| 4.9** | IV-4 | 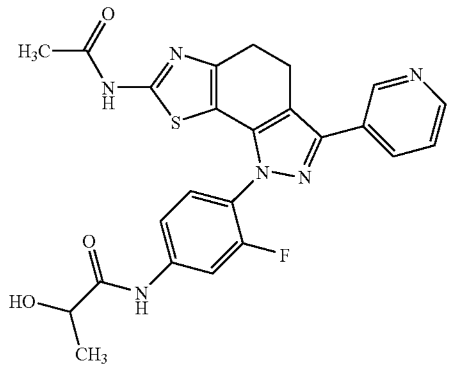 | 493 | 1.47 |
| 4.10 | IV-4 | 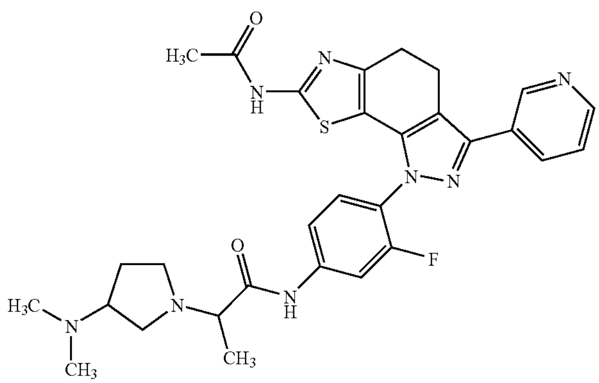 | 589 | 1.2 |
| 4.11 | IV-4 | 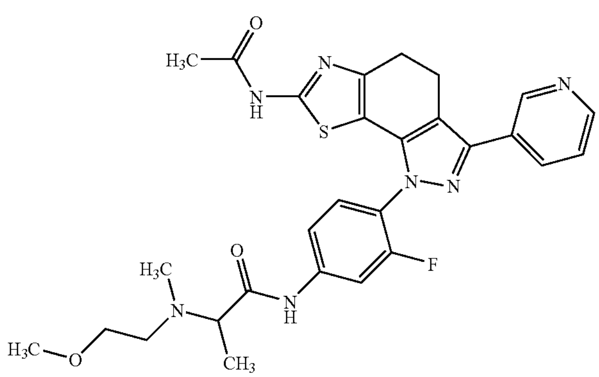 | 564 | 1.32 |
| 4.13 | IV-4 | 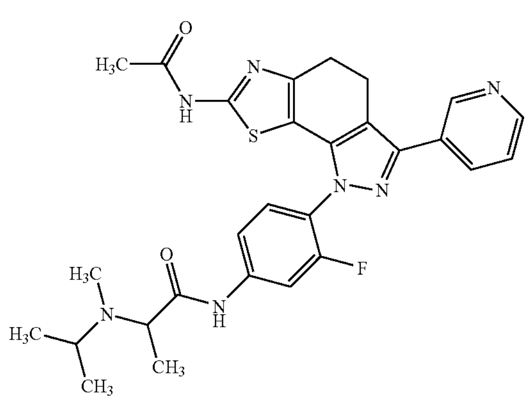 | 548 | 1.31 |

-continued

| # | educt | structure | mass [M + 1]⁺ | HPLC Rt [min] |
|---|---|---|---|---|
| 4.14 | IV-4 | 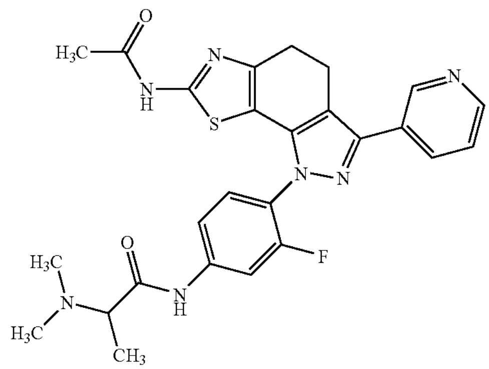 | 520 | 1.31 |
| 4.15 | IV-4 | 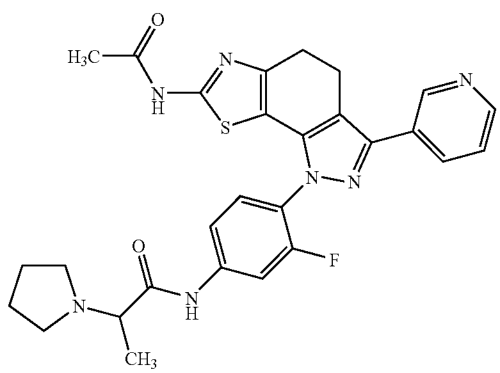 | 546 | 1.32 |
| 4.16 | IV-4 | 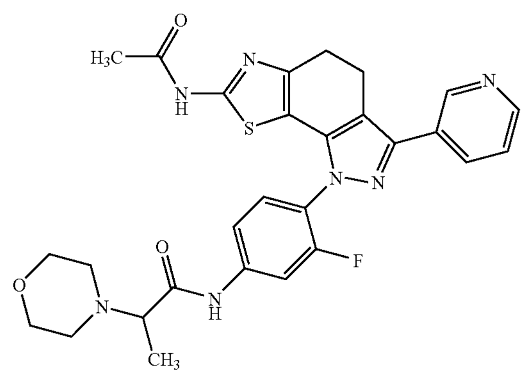 | 562 | 1.28 |
| 4.17 | IV-2 | 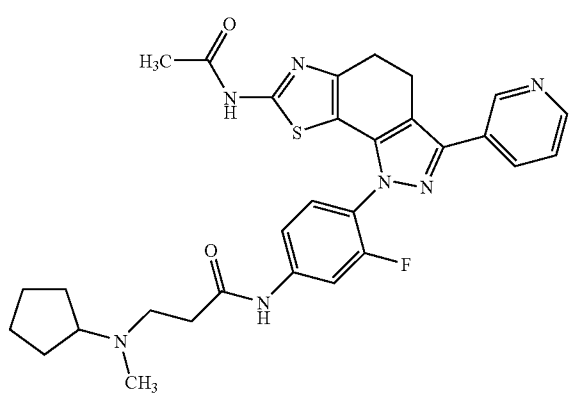 | 574 | 1.39 |

-continued

| # | educt | structure | mass [M + 1]+ | HPLC Rt [min] |
|---|---|---|---|---|
| 4.18 | IV-2 | 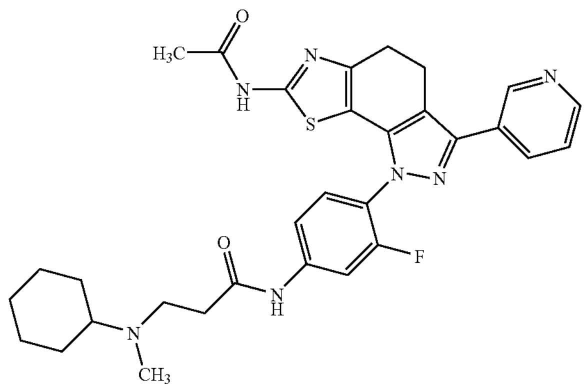 | 588 | 1.43 |
| 4.19 | IV-2 | 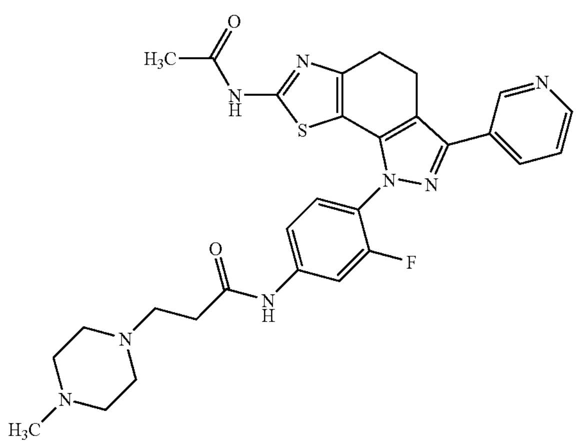 | 575 | 1.29 |
| 4.20 | IV-2 | 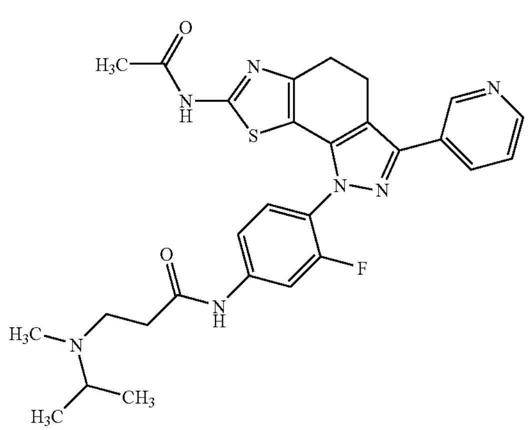 | 548 | 1.4 |

-continued

| # | educt | structure | mass [M + 1]+ | HPLC Rt [min] |
|---|---|---|---|---|
| 4.21 | IV-2 | (structure) | 546 | 1.36 |
| 4.22 | IV-2 | (structure) | 562 | 1.34 |

*Example 4.8 is obtained as a by-product of the reaction IV-3 with dimethylamine.
**Example 4.9 is obtained as a by-product of the reaction of IV-4 with N, O-dimethylhydroxylamine hydrochloride.

The following substances are synthesised analogously to the Examples described hereinbefore.

91
-continued
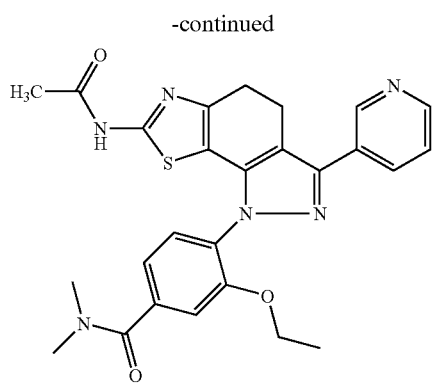
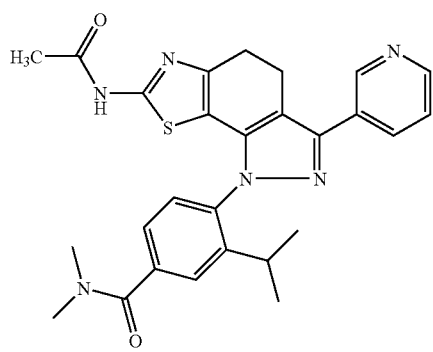
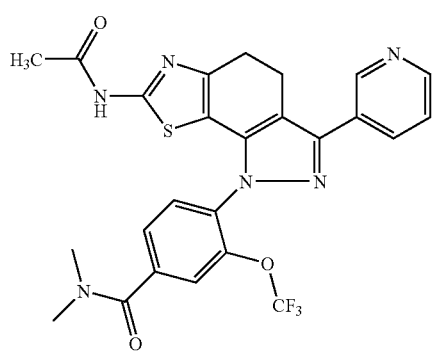
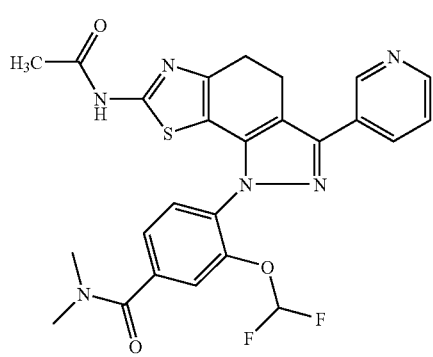
92
-continued
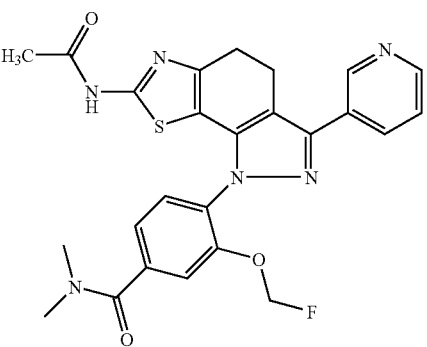
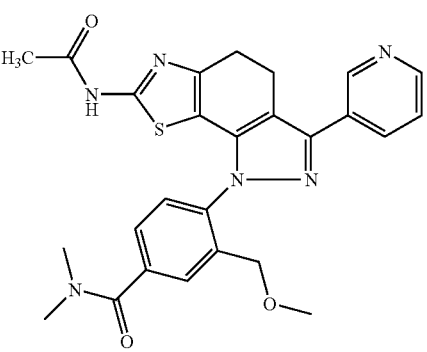
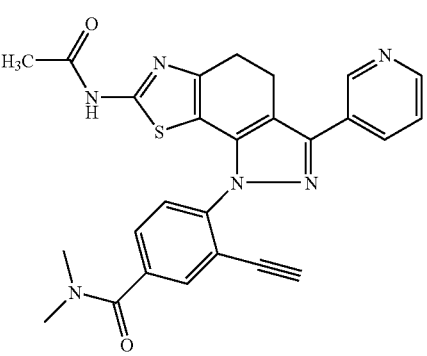
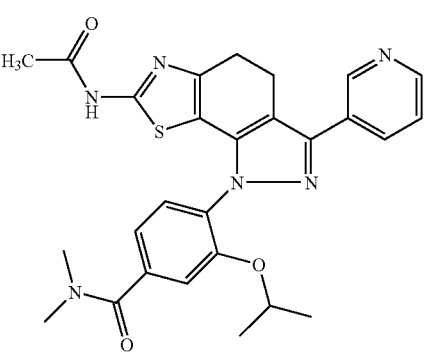

-continued
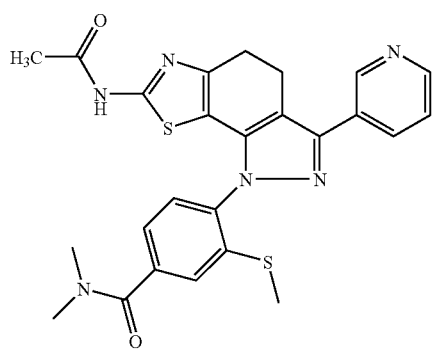
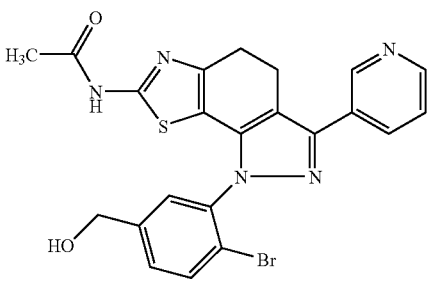
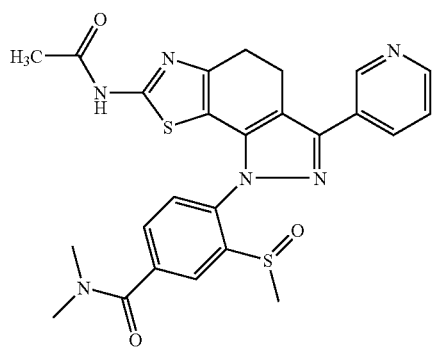
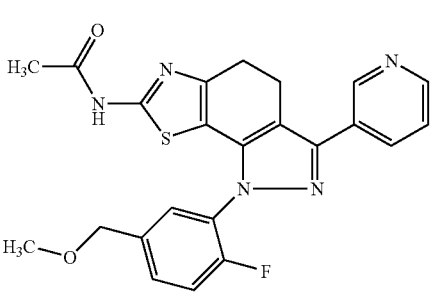
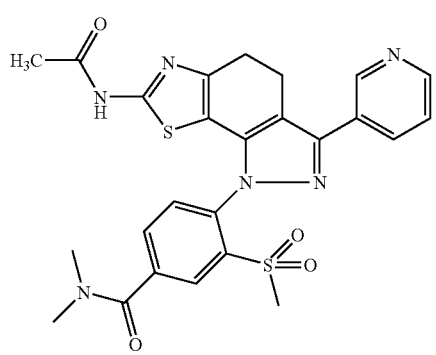
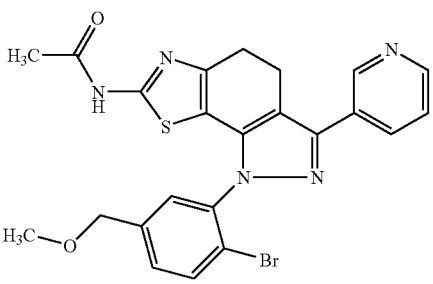
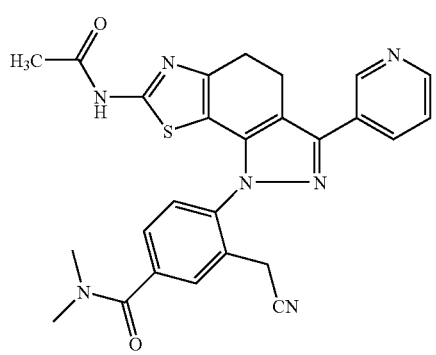
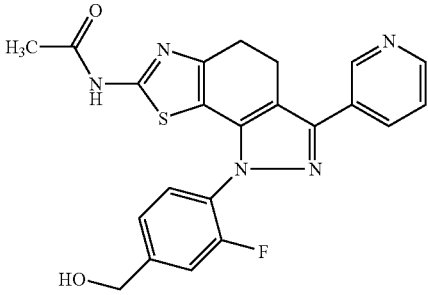
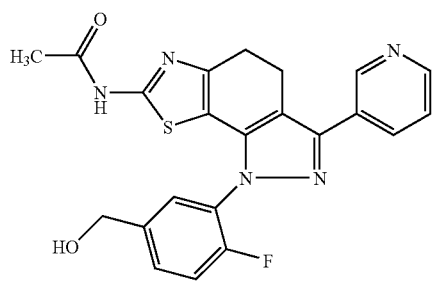
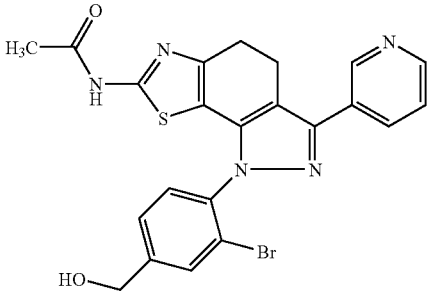

95
-continued
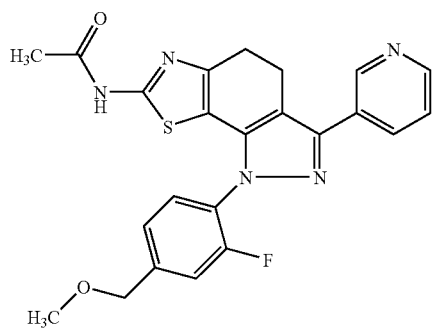
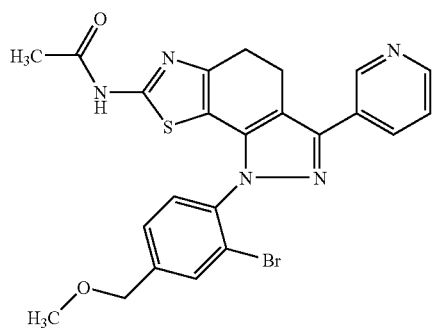
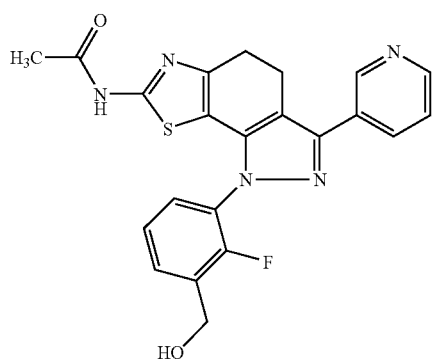
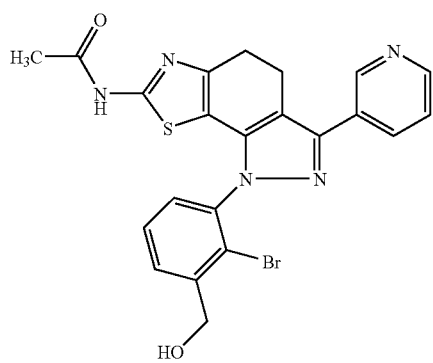
96
-continued
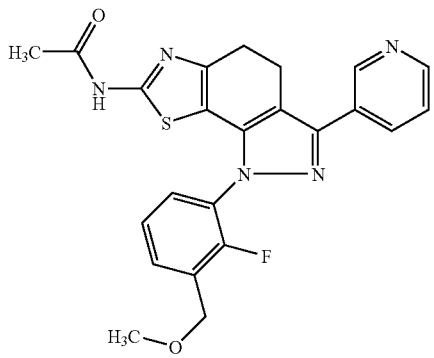
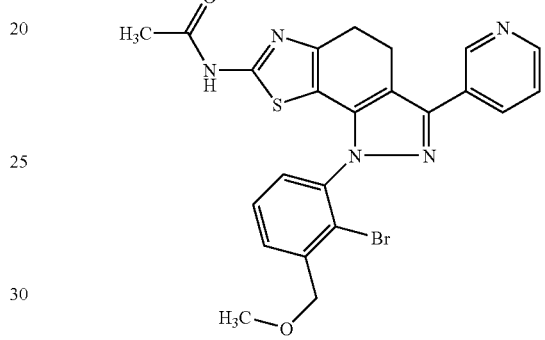
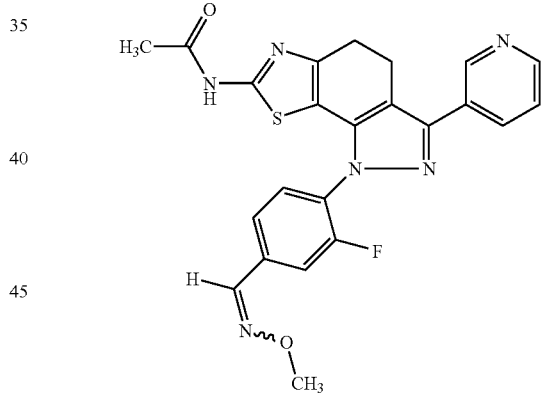
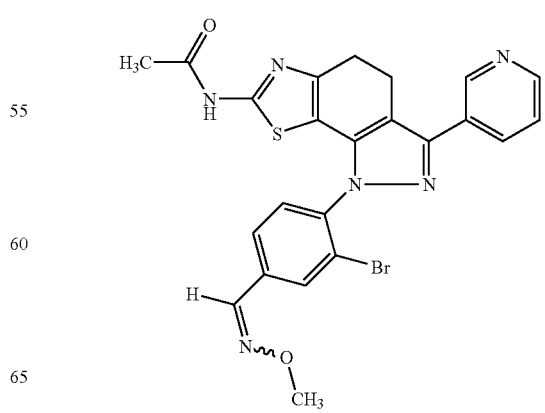

97
-continued
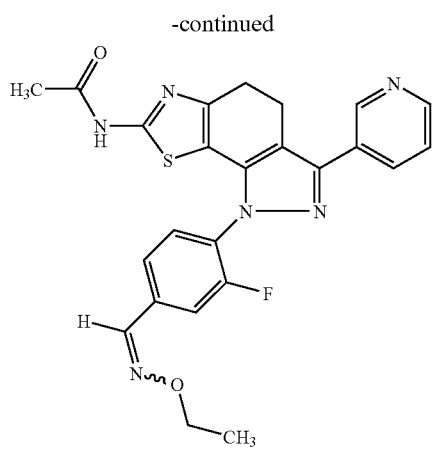
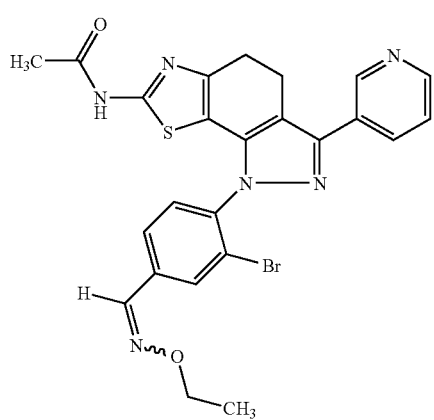
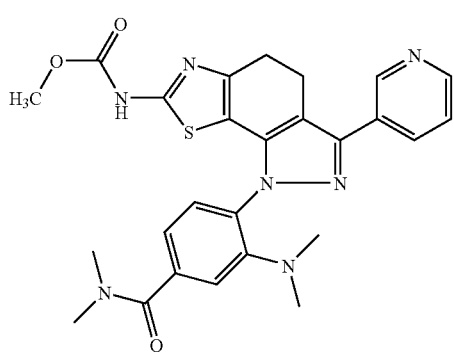
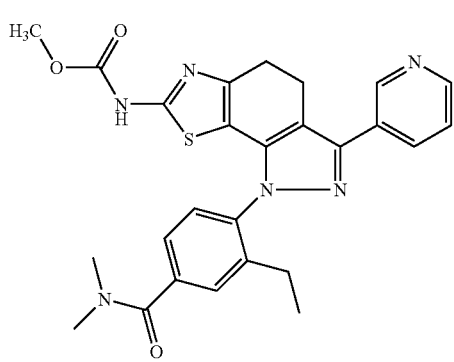
98
-continued
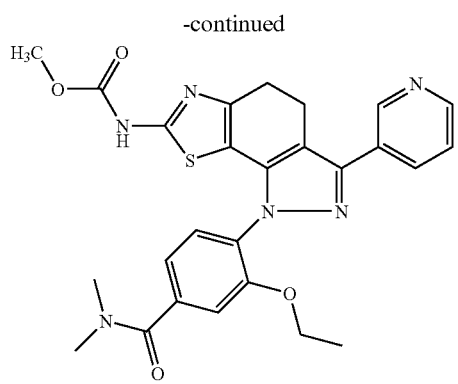
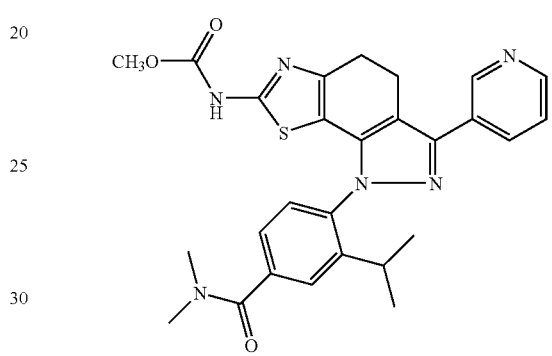
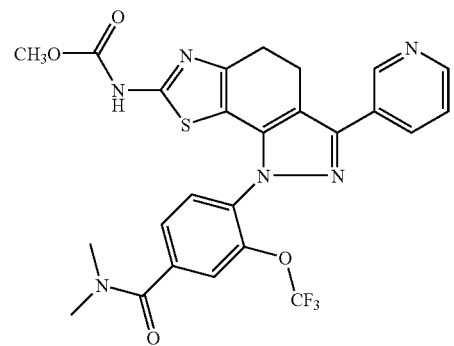
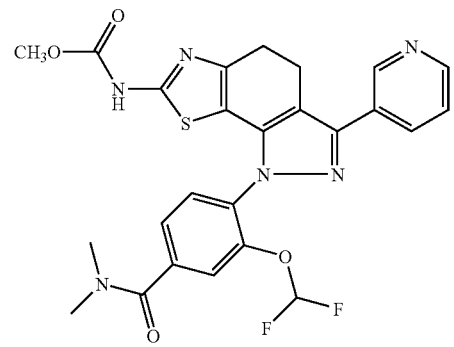

99
-continued
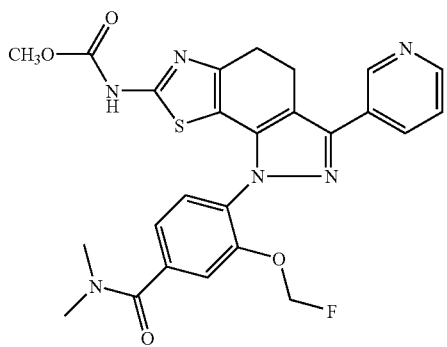
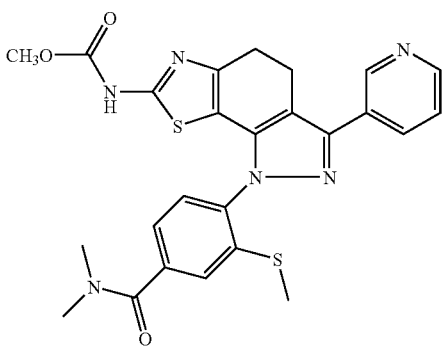
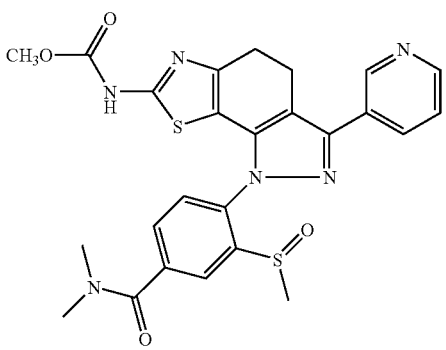
100
-continued
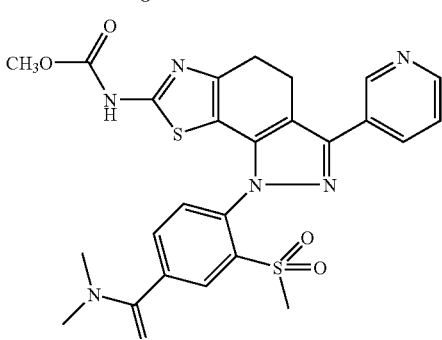
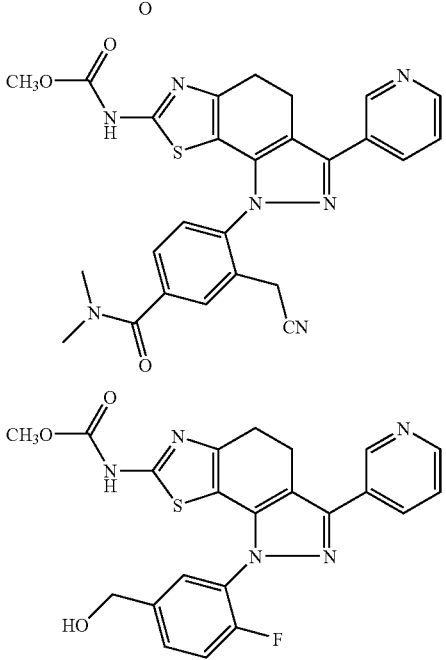

-continued
| 101 | 102 |
|---|---|
| 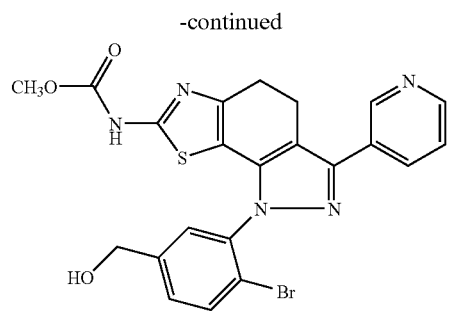 | 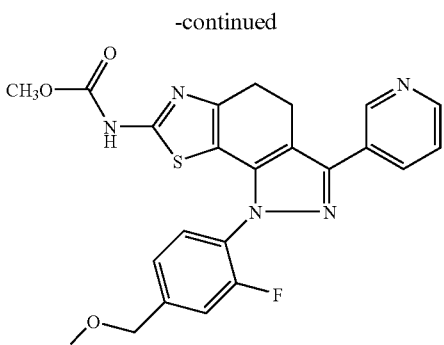 |
| 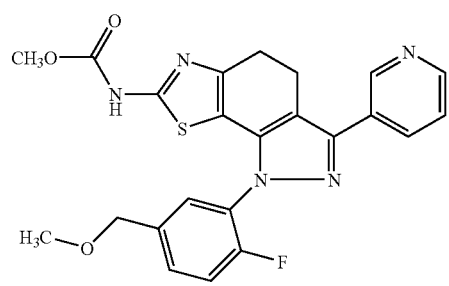 | 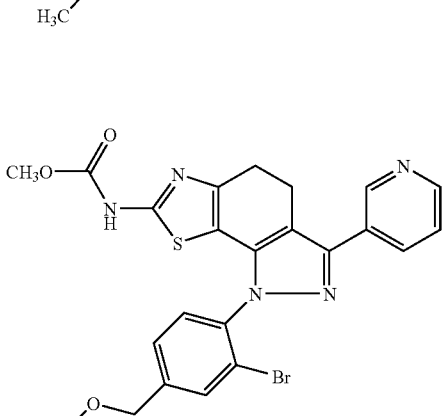 |
| 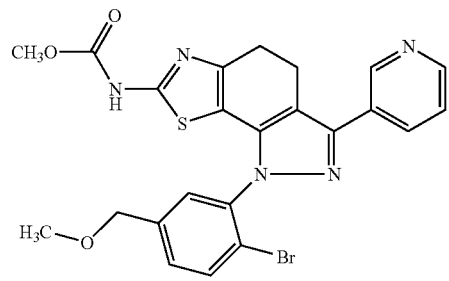 | 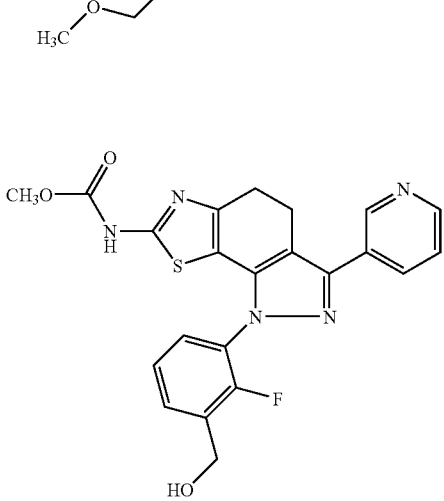 |
| 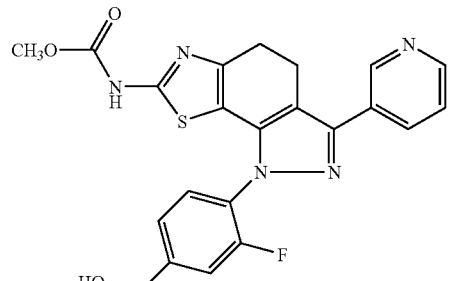 | |
| 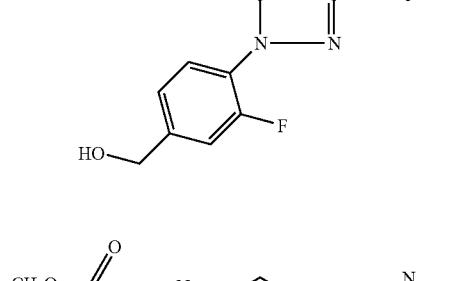 | 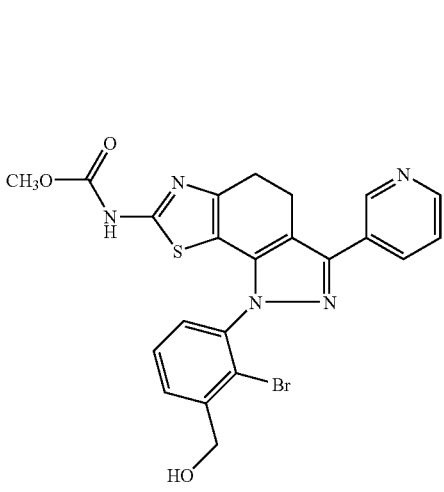 |
| 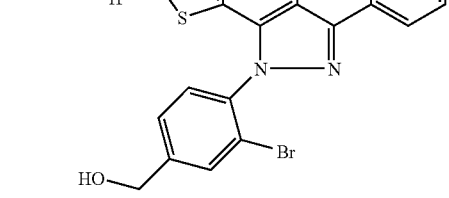 | |

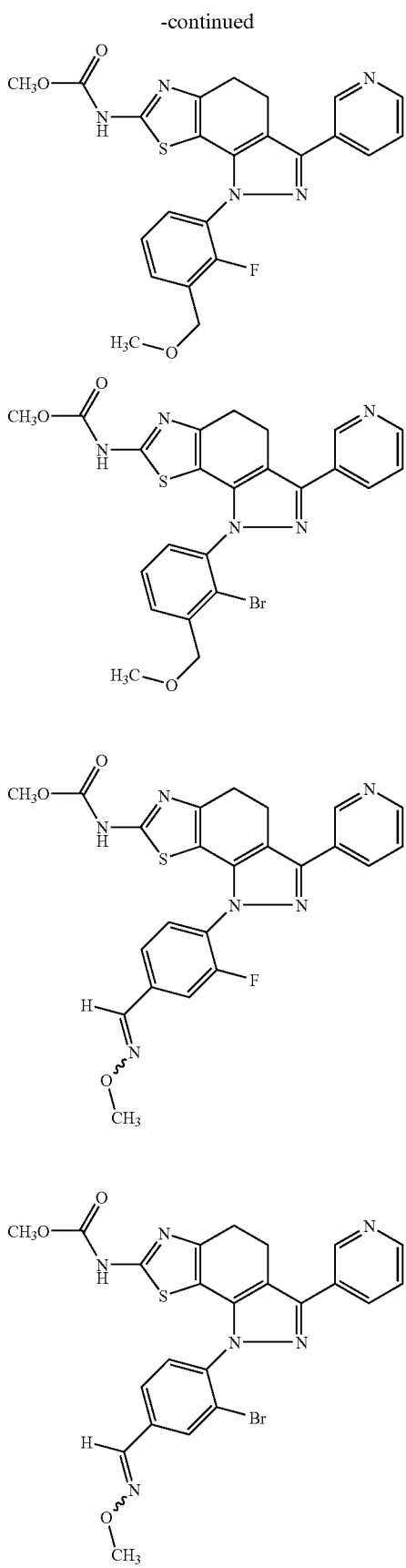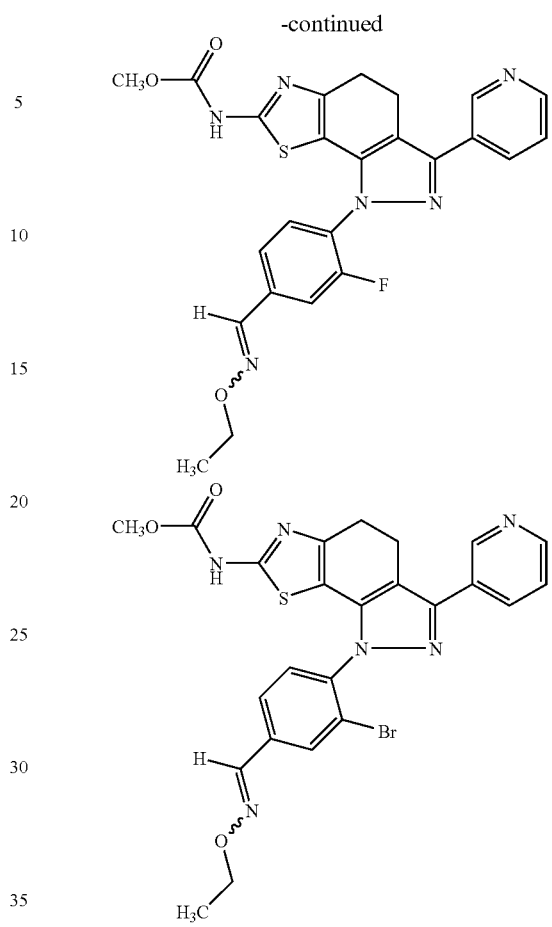

The Example that follows describes the biological activity of the compounds according to the invention without restricting the invention to this Example.

HCT116 Cytotoxicity Test

The test is based on the reduction of AlamarBlue (Biosource Int., USA) in living (metabolically active) cells to give a fluorometrically detectable product. The substrate can no longer be reduced in the presence of substances which are toxic to the cells, which means that it is not possible to measure any increase in fluorescence.

HCT116 (human colon carcinoma cell line) cells are sown in microtitre plates and incubated overnight in culture medium at 37° C. and 5% $CO_2$. The test substances are diluted stepwise in medium and added to the cells such that the total volume is 200 μl/well. Cells to which medium, but not substance, is added serve as controls. After an incubation time of 4-6 days, 20 μl of AlamarBlue are added/well and the cells are incubated at 37° C. for a further 6-8 h. For measuring the fluorescence, excitation takes place at a wavelength of 545 nm and the emission is measured at 590 nm.

$EC_{50}$ values are calculated using the GraphPad Prism program.

All the compounds of Examples 1.1 to 4.22 cited have an $EC_{50}$ (HCT-116) of less than 5 μM.

The substances of the present invention are PI3 kinase inhibitors. On account of their biological properties, the novel compounds of the general formula (1) and their isomers and their physiologically tolerated salts are suitable for treating diseases which are characterized by excessive or anomalous cell proliferation.

These diseases include, for example: viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphomas and solid tumours; skin diseases (e.g. psoriasis); bone diseases; cardiovascular diseases (e.g. restenosis and hypertrophy). In addition, the compounds are useful for protecting proliferating cells (e.g. hair cells, intestinal cells, blood cells and progenitor cells) from DNA damage due to irradiation, UV treatment and/or cytostatic treatment (Davis et al., 2001).

For example, the following cancer diseases can be treated with compounds according to the invention, without, however, being restricted thereto: brain tumours, such as acoustic neurinoma, astrocytomas such as piloid astrocytomas, fibrillary astrocytoma, protoplasmic astrocytoma, gemistocytic astrocytoma, anaplastic astrocytoma and glioblastomas, brain lymphomas, brain metastases, hypophyseal tumour such as prolactinoma, HGH (human growth hormone) producing tumour and ACTH-producing tumour (adrenocorticotrophic hormone), craniopharyngiomas, medulloblastomas, meningiomas and oligodendrogliomas; nerve tumours (neoplasms) such as tumours of the vegetative nervous system such as neuroblastoma sympathicum, ganglioneuroma, paraganglioma (phaeochromocytoma and chromaffinoma) and glomus caroticum tumour, tumours in the peripheral nervous system such as amputation neuroma, neurofibroma, neurinoma (neurilemoma, schwannoma) and malignant schwannoma, as well as tumours in the central nervous system such as brain and spinal cord tumours; intestinal cancer such as rectal carcinoma, colon carcinoma, anal carcinoma, small intestine tumours and duodenal tumours; eyelid tumours such as basalioma or basal cell carcinoma; pancreatic gland cancer or pancreatic carcinoma; bladder cancer or bladder carcinoma; lung cancer (bronchial carcinoma) such as small-cell bronchial carcinomas (oat cell carcinomas) and non-small-cell bronchial carcinomas such as squamous epithelium carcinomas, adenocarcinomas and large-cell bronchial carcinomas; breast cancer such as mammary carcinoma, such as infiltrating ductal carcinoma, colloid carcinoma, lobular invasive carcinoma, tubular carcinoma, adenoid cystic carcinoma, and papillary carcinoma; non-Hodgkin's lymphomas (NHL) such as Burkitt's lymphoma, low-malignancy non-Hodkgin's lymphomas (NHL) and mucosis fungoides; uterine cancer or endometrial carcinoma or corpus carcinoma; CUP syndrome (cancer of unknown primary); ovarian cancer or ovarian carcinoma such as mucinous, endometrial or serous cancer; gall bladder cancer; bile duct cancer such as Klatskin's tumour; testicular cancer such as seminomas and non-seminomas; lymphoma (lymphosarcoma) such as malignant lymphoma, Hodgkin's disease, non-Hodgkin's lymphomas (NHL) such as chronic lymphatic leukaemia, hair cell leukaemia, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as vocal cord tumours, supraglottal, glottal and subglottal laryngeal tumours; bone cancer such as osteochondroma, chondroma, chrondoblastoma, chondromyxoidfibroma, osteoma, osteoid-osteoma, osteoblastoma, eosinophilic granuloma, giant cell tumour, chondrosarcoma, osteosarcoma, Ewing's sarcoma, reticulosarcoma, plasmocytoma, fibrous dysplasia, juvenile bone cyst and aneurysmatic bone cyst; head/neck tumours such as tumours of the lips, tongue, floor of the mouth, oral cavity, gingiva, pallet, salivary glands, pharynx, nasal cavities, paranasal sinuses, larynx and middle ear; liver cancer such as liver cell carcinoma or hepatocellular carcinoma (HCC); leukaemias, such as acute leukaemias, such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or stomach carcinoma such as papillary, tubular and mucinous adenocarcinoma, signet ring cell carcinoma, adenoid squamous cell carcinoma, small-cell carcinoma and undifferentiated carcinoma; melanomas such as superficially spreading, nodular malignant lentigo and acral lentiginous melanoma; renal cancer, such as kidney cell carcinoma or hypernephroma or Grawitz's tumour; oesophageal cancer or oesophageal carcinoma; cancer of the penis; prostate cancer; pharyngeal cancer or pharyngeal carcinomas such as nasopharyngeal carcinomas, oropharyngeal carcinomas and hypopharyngeal carcinomas; retinoblastoma such as vaginal cancer or vaginal carcinoma; squamous epithelium carcinomas, adeno carcinomas, in situ carcinomas, malignant melanomas and sarcomas; thyroid gland carcinomas such as papillary, follicular and medullary thyroid gland carcinoma, and also anaplastic carcinomas; spinalioma, prickle cell carcinoma and squamous epithelium carcinoma of the skin; thymomas, urethral cancer and vulvar cancer.

The novel compounds can be used for the prevention or short-term or long-term treatment of the abovementioned diseases including, where appropriate, in combination with other state-of-the-art compounds such as other anti-tumour substances, cytotoxic substances, cell proliferation inhibitors, antiangiogenic substances, steroids or antibodies.

The compounds of the general formula (1) can be used on their own or in combination with other active compounds according to the invention and, where appropriate, in combination with other pharmacologically active compounds as well. Chemotherapeutic agents which can be administered in combination with the compounds according to the invention include, without being restricted thereto, hormones, hormone analogs and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone and octreotide), aromatase inhibitors (e.g. anastrozole, letrozole, liarozole, vorozole, exemestane and atamestane), LHRH agonists and antagonists (e.g. goserelin acetate and luprolide), inhibitors of growth factors (growth factors such as platelet-derived growth factor and hepatocyte growth factor, examples of inhibitors are growth factor antibodies, growth factor receptor antibodies and tyrosine kinase inhibitors, such as gefitinib, imatinib, lapatinib and trastuzumab); antimetabolites (e.g. antifolates such as methotrexate and raltitrexed, pyrimidine analogs such as 5-fluorouracil, capecitabine and gemcitabine, purine and adenosine analogs such as mercaptopurine, thioguanine, cladribine and pentostatin, cytarabine and fludarabine); antitumour antibiotics (e.g. anthracyclines, such as doxorubicin, daunorubicin, epirubicin and idarubicin, mitomycin C, bleomycin, dactinomycin, plicamycin and streptozocin); platinum derivatives (e.g. cisplatin, oxaliplatin and carboplatin); alkylating agents (e.g. estramustine, mechlorethamine, melphalan, chlorambucil, busulphan, dacarbazine, cyclophosphamide, ifosfamide and temozolomide, nitrosoureas such as carmustine and lomustine and thiotepa); antimitotic agents (e.g. vinca alkaloids such as vinblastine, vindesine, vinorelbine and vincristine; and taxans such as paclitaxel and docetaxel); topoisomerase inhibitors (e.g. epipodophyllotoxins such as etoposide and etopophos, teniposide, amsacrine, topotecan, irinotecan and mitoxantrone) and various chemotherapeutic agents such as amifostin, anagrelide, clodronate, filgrastin, interferon alpha, leucovorin, rituximab, procarbazine, levamisole, mesna, mitotan, pamidronate and porfimer.

Examples of suitable forms for use are tablets, capsules, suppositories, solutions, in particular solutions for injection (s.c., i.v., i.m.) and infusion, syrups, emulsions or dispersible powders. In this connection, the proportion of the pharmaceutically active compound(s) should in each case be in the range of 0.1-90% by weight, preferably 0.5-50% by weight, of the total composition, that is in quantities which are sufficient to achieve the dosage range which is specified below. If necessary, the doses mentioned can be given several times a day.

Appropriate tablets can be obtained, for example, by mixing the active compound(s) with known auxiliary substances, for example inert diluents, such as calcium carbonate, calcium phosphate or lactose, disintegrants, such as maize starch or alginic acid, binders, such as starch or gelatine, lubricants, such as magnesium stearate or talc, and/or agents for achieving a depot effect, such as carboxymethyl cellulose, cellulose acetate phthalate or polyvinyl acetate. The tablets can also comprise several layers.

Correspondingly, sugar-coated tablets can be produced by coating cores, which have been prepared in analogy with tablets, with agents which are customarily used in sugar coatings, for example collidone or shellac, gum arabic, talc, titanium dioxide or sugar. The core can also comprise several layers in order to achieve a depot effect or to avoid incompatibilities. In the same way, the sugar coating can also comprise several layers in order to achieve a depot effect, with it being possible to use the auxiliary substances which are mentioned above in the case of the tablets.

Syrups of the active compounds or active compound combinations according to the invention can additionally comprise a sweetening agent, such as saccharine, cyclamate, glycerol or sugar as well as a taste-improving agent, e.g. flavouring agents such as vanillin or orange extract. They can also comprise suspension aids or thickeners, such as sodium carboxymethyl cellulose, wetting agents, for example condensation products of fatty alcohols and ethylene oxide, or protectants such as p-hydroxybenzoates.

Injection and infusion solutions are produced in a customary manner, e.g. while adding isotonizing agents, preservatives, such as p-hydroxybenzoates, or stabilizers, such as alkali metal salts of ethylenediaminetetraacetic acid, where appropriate using emulsifiers and/or dispersants, with it being possible, for example, to employ, where appropriate, organic solvents as solubilizing agents or auxiliary solvents when using water as diluent, and aliquoted into injection bottles or ampoules or infusion bottles.

The capsules, which comprise one or more active compounds or active compound combinations, can, for example, be produced by mixing the active compounds with inert carriers, such as lactose or sorbitol, and encapsulating the mixture in gelatine capsules. Suitable suppositories can be produced, for example, by mixing with excipients which are envisaged for this purpose, such as neutral fats or polyethylene glycol, or their derivatives.

Auxiliary substances which may be mentioned by way of example are water, pharmaceutically unobjectionable organic solvents, such as paraffins (e.g. petroleum fractions), oils of vegetable origin (e.g. groundnut oil or sesame oil), monofunctional or polyfunctional alcohols (e.g. ethanol or glycerol), carrier substances such as natural mineral powders (e.g. kaolins, argillaceous earths, talc and chalk), synthetic mineral powders (e.g. highly disperse silicic acid and silicates), sugars (e.g. cane sugar, lactose and grape sugar), emulsifiers (e.g. lignin, sulphite waste liquors, methyl cellulose, starch and polyvinylpyrrolidone) and glidants (e.g. magnesium stearate, talc, stearic acid and sodium lauryl sulphate).

Administration is effected in a customary manner, preferably orally or transdermally, in particular and preferably orally. In the case of oral use, the tablets can naturally also comprise, in addition to the abovementioned carrier substances, additives such as sodium citrate, calcium carbonate and dicalcium phosphate together with a variety of further substances such as starch, preferably potato starch, gelatine and the like. It is furthermore also possible to use glidants, such as magnesium stearate, sodium lauryl sulphate and talc, for the tableting. In the case of aqueous suspensions, a variety of taste improvers or dyes can also be added to the active compounds in addition to the abovementioned auxiliary substances.

For parenteral administration, it is possible to employ solutions of the active compounds while using suitable liquid carrier materials. The dosage for intravenous administration is 1-1000 mg per hour, preferably between 5 and 500 mg per hour.

Despite this, it may be necessary, where appropriate, to diverge from the abovementioned quantities, depending on the body weight or the nature of the route of administration, on the individual response to the medicament, on the nature of its formulation and on the time or interval at which the administration is effected. Thus, it may, in some cases, be sufficient to make do with less than the previously mentioned lowest quantity whereas, in other cases, the abovementioned upper limit has to be exceeded. When relatively large quantities are being administered, it may be advisable to divide these into several single doses which are given over the course of the day.

The following formulation examples illustrate the present invention without, however, restricting its scope:

Pharmaceutical Formulation Examples

| A) Tablets | per tablet |
| --- | --- |
| Active compound in accordance with formula (1) | 100 mg |
| Lactose | 140 mg |
| Maize starch | 240 mg |
| Polyvinylpyrrolidone | 15 mg |
| Magnesium stearate | 5 mg |
| | 500 mg |

The finely ground active compound, lactose and a part of the maize starch are mixed with each other. The mixture is sieved, after which it is moistened with a solution of polyvinylpyrrolidone in water, kneaded, wet-granulated and dried. The granular material, the remainder of the maize starch and the magnesium stearate are sieved and mixed with each other. The mixture is pressed into tablets of suitable shape and size.

| B) Tablets | per tablet |
| --- | --- |
| Active compound in accordance with formula (1) | 80 mg |
| Lactose | 55 mg |

-continued

| B) Tablets | per tablet |
|---|---|
| Maize starch | 190 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active compound, a part of the maize starch, the lactose, microcrystalline cellulose and polyvinylpyrrolidone are mixed with each other, after which the mixture is sieved and worked, together with the remainder of the maize starch and water, into a granular material, which is dried and sieved. The sodium carboxymethyl starch and the magnesium stearate are then added to the granular material and mixed with it, and the mixture is pressed into tablets of suitable size.

| C) Ampoule solution | |
|---|---|
| Active compound in accordance with formula (1) | 50 mg |
| Sodium chloride | 50 mg |
| Water for injection | 5 ml |

The active compound is dissolved, either at its intrinsic pH or, where appropriate, at pH 5.5-6.5, in water after which sodium chloride is added as isotonizing agent. The resulting solution is rendered pyrogen-free by filtration and the filtrate is aliquoted, under aseptic conditions, into ampoules, which are then sterilized and sealed by melting. The ampoules contain 5 mg, 25 mg and 50 mg of active compound.

What is claimed is:
1. A compound of formula (1),

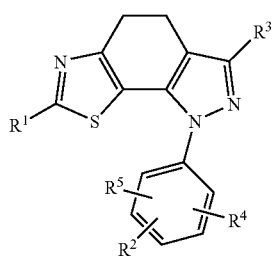

(1)

wherein
$R^1$ is selected from among —$NHR^c$, —$NHC(O)R^c$, —$NHC(O)OR^c$, —$NHC(O)NR^cR^c$ and —$NHC(O)SR^c$, and
$R^2$ denotes $C_{1-6}$alkyl or 3-8 membered heterocycloalkyl, optionally substituted by one or more $R^6$, or a group selected from among halogen, —$NO_2$, —$NR^cR^c$, —$OR^c$, —$S(O)R^c$, —$S(O)_2R^c$, —$C(O)R^c$, —$C(O)OR^c$, —$C(O)NR^cR^c$, —$C(O)N(R^g)OR^c$—$N(R^g)C(O)R^c$, —$N(R^g)C(O)OR^c$, —$NR^gC(O)NR^cR^c$, —$N(R^g)C(O)SR^c$ and —$N(R^g)S(O)_2R^c$, and
$R^3$ denotes a group selected from among $C_{6-10}$aryl and 5-6 membered heteroaryl, optionally substituted by one or more, identical or different $R^c$ and/or $R^b$, and
$R^4$ denotes a group selected from among bromine, fluorine, —$CF_3$, —$OCF_3$, —$CN$, —$NR^cR^c$, —$SR^c$, —$S(O)R^c$, —$S(O)_2R^c$ and —$OR^c$, or $C_{1-3}$alkyl optionally substituted by fluorine, —$CN$, —$NR^fR^f$ and/or —$OR^f$, and
$R^5$ denotes hydrogen or a group selected from among halogen, —$CF_3$, —$OCF_3$, —$CN$, —$NR^cR^c$, —$SR^c$, —$S(O)R^c$, —$S(O)_2R^c$ and —$OR^c$, or $C_{1-3}$alkyl optionally substituted by fluorine, —$CN$, —$NR^fR^f$ and/or —$OR^f$, and
$R^6$ denotes a group selected from among $R^a$, $R^b$ and $R^a$ substituted by one or more, identical or different $R^c$ and/or $R^b$, and
each $R^a$ independently of one another is selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, and
each $R^b$ denotes a suitable group each independently selected from among =O, —$OR^c$, $C_{1-3}$haloalkyloxy, —$OCF_3$, =S, —$SR^c$, =$NR^c$, =$NOR^c$, —$NR^cR^c$, halogen, —$CF_3$, —$CN$, —$NC$, —$NO_2$, —$N_3$, —$S(O)R^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)_2NR^cR^c$, —$C(O)R^c$, —$C(O)OR^c$, —$C(O)NR^cR^c$, —$C(O)N(R^g)NR^cR^c$, —$C(O)N(R^g)OR^c$, —$CN(R^g)NR^cR^c$, —$OC(O)R^c$, —$OC(O)OR^c$, —$OC(O)NR^cR^c$, —$N(R^g)C(O)R^c$, —$N(R^g)C(O)R^c$, —$N(R^g)C(S)R^c$, —$N(R^g)S(O)_2R^c$, —$N(R^g)S(O)_2NR^cR^c$, —$N(R^g)C(O)OR^c$, —$N(R^g)C(O)NR^cR^c$, and —$N(R^g)CN(R^g)NR^cR^c$, and
each $R^c$ independently of one another denotes hydrogen or a group optionally substituted by one or more, identical or different $R^d$ and/or $R^e$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, and
each $R^d$ independently of one another denotes a group optionally substituted by one or more, identical or different $R^e$ and/or $R^f$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, and
each $R^e$ denotes a suitable group each independently selected from among =O, —$OR^f$, $C_{1-3}$haloalkyloxy, —$OCF_3$, =S, —$SR^f$, =$NR^f$, =$NOR^f$, —$NR^fR^f$, halogen, —$CF_3$, —$CN$, —$NC$, —$NO_2$, —$N_3$, —$S(O)R^f$, —$S(O)_2R^f$, —$S(O)_2OR^f$, —$S(O)NR^fR^f$, —$S(O)_2NR^fR^f$, —$OS(O)R^f$, —$OS(O)_2R^f$, —$OS(O)_2OR^f$, —$OS(O)_2NR^fR^f$, —$C(O)R^f$, —$C(O)OR^f$, —$C(O)NR^fR^f$, —$C(O)N(R^g)OR^f$, —$CN(R^g)NR^fR^f$, —$OC(O)R^f$, —$OC(O)OR^f$, —$OC(O)NR^fR^f$, —$OCN(R^g)NR^fR^f$, —$N(R^g)C(O)R^f$, —$N(R^g)C(S)R^f$, —$N(R^g)S(O)_2R^f$, —$N(R^g)C(O)OR^f$, —$N(R^g)C(O)NR^fR^f$, and —$N(R^g)CN(R^g)NR^fR^f$, and
each $R^f$ independently of one another denotes hydrogen or a group optionally substituted by one or more, identical or different $R^g$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, and
each $R^g$ independently of one another denotes hydrogen, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, or a pharmacologically acceptable salt thereof, with the proviso that the following compounds are not included:

4-(7-acetylamino-3-pyridin-3-yl-4,5-dihydro-pyrazolo[4,3-g]benzothiazol-1-yl)-3-fluoro-N-(2-methoxy-ethyl)-N-methyl-benzamide, N-{1-[2-fluoro-4-(morpholino-4-carbonyl)-phenyl]-3-pyridin-3-yl-4,5-dihydro-1H-pyrazolo[4,3-g]benzothiazol-7-yl}-acetamide, 4-(7-acetylamino-3-pyridin-3-yl-4,5-dihydro-pyrazolo[4,3-g]benzothiazol-1-yl)-3-fluoro-N,N-dimethyl-benzamide, 4-(7-acetylamino-3-pyridin-3-yl-4,5-dihydro-pyrazolo[4,3-g]benzothiazol-1-yl)-N-ethyl-3-fluoro-N-methyl-benzamide, 4-(7-acetylamino-3-pyridin-3-yl-4,5-dihydro-pyrazolo[4,3-g]benzothiazol-1-yl)-N-ethyl-3-fluoro-N-(2-methoxy-ethyl)-benzamide, N-{1-[2-fluoro-4-([1.4]oxazepan-4-carbonyl)-phenyl]-3-pyridin-3-yl-4,5-dihydro-1H-pyrazolo[4,3-g]benzothiazol-7-yl}-acetamide, 4-(7-acetylamino-3-pyrazin-3-yl-4,5-dihydro-pyrazolo[4,3-g]benzothiazol-1-yl)-3,N,N-trimethyl-benzamide, 4-(7-acetylamino-3-pyridin-3-yl-4,5-dihydro-pyrazolo[4,3-g]benzothiazol-1-yl)-2-methoxy-N-(4-pyrrolidin-1-yl-cyclohexyl)-benzamide, 4-(7-acetylamino-3-pyridin-3-yl-4,5-dihydro-pyrazolo[4,3-g]benzothiazol-1-yl)-2-methoxy-N-methyl-N-(4-pyrrolidin-1-yl-cyclohexyl)-benzamide, 4-(7-acetylamino-3-pyridin-3-yl-4,5-dihydro-pyrazolo[4,3-g]benzothiazol-1-yl)-N-(1-cyclopentyl-piperidin-4-yl)-2-methoxy-benzamide, 4-(7-acetylamino-3-pyridin-3-yl-4,5-dihydro-pyrazolo[4,3-g]benzothiazol-1-yl)-N-(1-cyclopentyl-piperidin-4-yl)-2-methoxy-N-methyl-benzamide, N-(1-{4-[4-(cyclopentyl-methyl-amino)-piperidine-1-carbonyl]-3-methoxy-phenyl}-3-pyridin-3-yl-4,5-dihydro-1H-pyrazolo[4,3-g]benzothiazol-7-yl)-acetamide, 4-(7-acetylamino-3-pyridin-3-yl-4,5-dihydro-pyrazolo[4,3-g]benzothiazol-1-yl)-N,N-diethyl-3-fluoro-benzamide, 4-(7-acetylamino-3-pyridin-3-yl-4,5-dihydro-pyrazolo[4,3-g]benzothiazol-1-yl)-3-fluoro-N-(2-methoxy-ethyl)-benzamide, 4-(7-acetylamino-3-pyridin-3-yl-4,5-dihydro-pyrazolo[4,3-g]benzothiazol-1-yl)-3-fluoro-N-(2-pyrrolidin-1-yl-ethyl)-benzamide, N-{1-[4-(4-dimethylamino-piperidine-1-carbonyl)-2-fluoro-phenyl]-3-pyridin-3-yl-4,5-dihydro-1H-pyrazolo[4,3-g]benzothiazol-7-yl}-acetamide, 4-(7-acetylamino-3-pyridin-3-yl-4,5-dihydro-pyrazolo[4,3-g]benzothiazol-1-yl)-3-fluoro-N-methyl-N-(1-methyl-piperidin-4-yl)-benzamide, 4-(7-acetylamino-3-pyridin-3-yl-4,5-dihydro-pyrazolo[4,3-g]benzothiazol-1-yl)-N-(2-dimethylamino-ethyl)-3-fluoro-benzamide, 4-(7-acetylamino-3-pyridin-3-yl-4,5-dihydro-pyrazolo[4,3-g]benzothiazol-1-yl)-N-(3-dimethylamino-propyl)-3-fluoro-N-methyl-benzamide, 4-(7-acetylamino-3-pyridin-3-yl-4,5-dihydro-pyrazolo[4,3-g]benzothiazol-1-yl)-N-(2-dimethylamino-ethyl)-3-fluoro-N-methyl-benzamide, N-{1-[2-fluoro-4-(4-isopropyl-piperazine-1-carbonyl)-phenyl]-3-pyridin-3-yl-4,5-dihydro-1H-pyrazolo[4,3-g]benzothiazol-7-yl}-acetamide, 4-(7-acetylamino-3-pyridin-3-yl-4,5-dihydro-pyrazolo[4,3-g]benzothiazol-1-yl)-N,N-diethyl-3-fluoro-benzamide, N-{1-[4-(4-cyclopentyl-piperazine-1-carbonyl)-2-fluoro-phenyl]-3-pyridin-3-yl-4,5-dihydro-1H-pyrazolo[4,3-g]benzothiazol-7-yl}-acetamide, N-(1-{4-[4-(1-ethyl-propyl)-piperazine-1-carbonyl]-2-fluoro-phenyl}-3-pyridin-3-yl-4,5-dihydro-1H-pyrazolo[4,3-g]benzothiazol-7-yl)-acetamide, N-{1-[4-(4-sec-butyl-piperazine-1-carbonyl)-2-fluoro-phenyl]-3-pyridin-3-yl-4,5-dihydro-1H-pyrazolo[4,3-g]benzothiazol-7-yl}-acetamide, 2-{4-[4-(7-acetylamino-3-pyridin-3-yl-4,5-dihydro-pyrazolo[4,3-g]benzothiazol-1-yl)-3-fluoro-benzoyl]-piperazin-1-yl}-N,N-dimethyl-acetamide, 4-(7-acetylamino-3-pyridin-3-yl-4,5-dihydro-pyrazolo[4,3-g]benzothiazol-1-yl)-3-fluoro-N-(3-morpholin-4-yl-cyclobutyl)-benzamide, N-{1-[2-fluoro-4-(4-methyl-piperazine-1-carbonyl)-phenyl]-3-pyridin-3-yl-4,5-dihydro-1H-pyrazolo[4,3-g]benzothiazol-7-yl}-acetamide, 4-(7-acetylamino-3-pyridin-3-yl-4,5-dihydro-pyrazolo[4,3-g]benzothiazol-1-yl)-3-fluoro-N,N-dimethyl-benzamide, N-[4-(7-acetylamino-3-pyridin-3-yl-4,5-dihydro-pyrazolo[4,3-g]benzothiazol-1-yl)-3-fluoro-phenyl]-2-dimethylamino-acetamide, N-[1-(4-acetylamino-2-fluoro-phenyl)-3-pyridin-3-yl-4,5-dihydro-1H-pyrazolo[4,3-g]benzothiazol-7-yl]-acetamide, 3-fluoro-4-[7-(3-methoxy-propionylamino)-3-pyridin-3-yl-4,5-dihydro-pyrazolo[4,3-g]benzothiazol-1-yl]-N,N-dimethyl-benzamide and 3-fluoro-N,N-dimethyl-4-[7-(3-phenyl-propionylamino)-3-pyridin-3-yl-4,5-dihydro-pyrazolo[4,3-g]benzothiazol-1-yl]benzamide.

2. A compound of claim 1, which is of formula (1A),

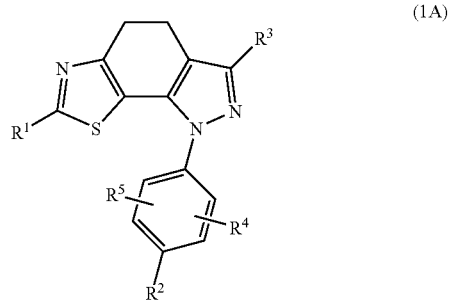

(1A)

wherein the substituents are defined as in claim 1.

3. A compound of claim 1, which is of formula (1B),

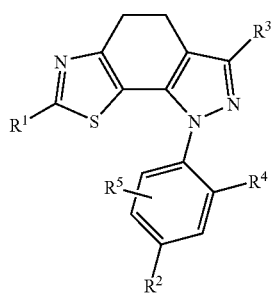

(1B)

wherein the substituents are defined as in claim 1.

4. A compound according to claim 1, wherein
R$^3$ denotes 5-6 membered heteroaryl, optionally substituted by one or more, identical or different R$^c$ and/or R$^b$.

5. A compound according to claim 1, wherein
R$^3$ denotes unsubstituted pyridyl.

6. A compound according to claim 1, wherein
R$^1$ is selected from among —NHC(O)OR$^c$ and —NHC(O)NR$^c$R$^c$.

7. A compound according to claim 1, wherein
R$^1$ denotes —NHC(O)R$^c$, and
R$^2$ denotes C$_{1-6}$alkyl or 3-8 membered heterocycloalkyl, optionally substituted by one or more R$^6$, or a group selected from among halogen, —NO$_2$, —NR$^c$R$^c$, —OR', —S(O)R$^c$, —S(O)$_2$R$^c$, —C(O)R$^c$, —C(O)OR$^c$, —N(R$^g$)C(O)R$^c$, —N(R$^g$)C(O)OR$^c$, —NR$^g$)C(O)NR$^c$R$^c$, —N(R$^g$)C(O)SR$^c$ and —N(R$^g$)S(O)$_2$R$^c$.

8. A pharmaceutical composition containing as active substance one or more compounds of formula (1) according to claim 1 or the pharmacologically effective salts thereof, optionally in combination with conventional excipients and/or carriers.

9. A pharmaceutical composition containing a compound of formula (1) according to claim 1 and at least one other cytostatic or cytotoxic active substance, different from formula (1), as well as optionally the pharmacologically acceptable salts thereof.

10. A method for preparing a medicament for the treatment of colon cancer, lung cancer or prostate cancer, which comprises bringing together a compound of formula (1) according to claim 1 together with conventional excipients and/or carriers suitable for providing a medicament.

11. A method for the treatment of colon cancer, lung cancer or prostate cancer, which comprises administering a compound of formula (1) according to claim 1 to a patient in need thereof.

* * * * *